(12) United States Patent
Lee et al.

(10) Patent No.: US 12,414,788 B2
(45) Date of Patent: *Sep. 16, 2025

(54) END TOOL OF SURGICAL INSTRUMENT AND SURGICAL INSTRUMENT INCLUDING THE SAME

(71) Applicant: LIVSMED INC., Seongnam-si (KR)

(72) Inventors: Jung Joo Lee, Yongin-si (KR); Hee Jin Kim, Seoul (KR); Dong Kyu Jang, Seoul (KR)

(73) Assignee: LIVSMED INC., Seongnam-si (KR)

( * ) Notice: Subject to any disclaimer, the term of this patent is extended or adjusted under 35 U.S.C. 154(b) by 944 days.

This patent is subject to a terminal disclaimer.

(21) Appl. No.: 17/553,127

(22) Filed: Dec. 16, 2021

(65) Prior Publication Data

US 2022/0104841 A1    Apr. 7, 2022

Related U.S. Application Data

(63) Continuation of application No. 17/059,418, filed as application No. PCT/KR2019/014557 on Oct. 31, 2019, now Pat. No. 11,278,302.

(51) Int. Cl.
*A61B 17/29* (2006.01)
*A61B 17/00* (2006.01)

(52) U.S. Cl.
CPC .... *A61B 17/29* (2013.01); *A61B 2017/00424* (2013.01); *A61B 2017/2903* (2013.01);
(Continued)

(58) Field of Classification Search
CPC . A61B 17/2912; A61B 17/2915; A61B 17/32; A61B 34/71; A61B 2017/2927;
(Continued)

(56) References Cited

U.S. PATENT DOCUMENTS 6,394,998 B1    5/2002   Wallace et al.
10,631,886 B2   4/2020   Lee et al.
(Continued)

FOREIGN PATENT DOCUMENTS

DE    102015118914 A1   5/2017
JP    1984-102587       6/1984
(Continued)

OTHER PUBLICATIONS

Office Action for EU Application No. 19950802.9, Jun. 2, 2023, Extended European Search Report.
(Continued)

*Primary Examiner* — Sarah W Aleman
(74) *Attorney, Agent, or Firm* — Bridgeway IP Law Group, PLLC; Sang Ho Lee; Hyun Woo Shin

(57) ABSTRACT

According to the present disclosure, provided is a surgical instrument in which an actual motion of bending an end tool or performing a surgical treatment intuitively matches a motion of a manipulation portion corresponding thereto. In detail, to this end, provided are an end tool having various degrees of freedom, a manipulation portion having a structure to enable intuitive manipulation of a motion of the end tool, and a driving force transmission portion for transmitting a driving force of the manipulation portion to the end tool so that the end tool operates as manipulated by the manipulation portion.

17 Claims, 23 Drawing Sheets

(52) U.S. Cl.
CPC .................. *A61B 2017/2912* (2013.01); *A61B 2017/2938* (2013.01)

(58) Field of Classification Search
CPC ...... A61B 2034/305; A61B 2017/2912; A61B 2017/2915; A61B 2017/32; A61B 17/29
See application file for complete search history.

(56) References Cited

U.S. PATENT DOCUMENTS

| | | | |
|---|---|---|---|
| 10,709,467 | B2 | 7/2020 | Lee et al. |
| 10,722,315 | B2 | 7/2020 | Lee et al. |
| 11,141,181 | B2 | 10/2021 | Scheltes |
| 2007/0088340 | A1 | 4/2007 | Brock et al. |
| 2007/0208375 | A1 | 9/2007 | Nishizawa et al. |
| 2010/0011901 | A1 | 1/2010 | Burbank |
| 2010/0016852 | A1 | 1/2010 | Manzo et al. |
| 2011/0106145 | A1 | 5/2011 | Jeong |
| 2015/0150635 | A1 | 6/2015 | Kilroy et al. |
| 2017/0042560 | A1 | 2/2017 | Lee et al. |
| 2020/0323601 | A1 | 10/2020 | Lee |

FOREIGN PATENT DOCUMENTS

| | | |
|---|---|---|
| JP | 1984-102587 A | 6/1984 |
| JP | 2010-220786 A | 10/2010 |
| JP | 2016-518160 A | 6/2016 |
| JP | 2017-513678 A | 6/2017 |
| JP | 2018-505001 A | 2/2018 |
| JP | 2018-149299 A | 9/2018 |
| JP | 2018-527094 A | 9/2018 |
| KR | 10-2010-0099818 A | 9/2010 |
| KR | 10-2011-0028613 A | 3/2011 |
| KR | 10-2013-0057250 A | 5/2013 |
| KR | 10-1772805 B1 | 8/2017 |
| WO | 2014/151952 A1 | 9/2014 |
| WO | 2018189721 A1 | 10/2018 |

OTHER PUBLICATIONS

Notice of Reasons for Refusal, Japanese Patent Application No. 2021-572472, Jul. 6, 2023, Ikimura, Tatsuto 3616 3I00.
Notice of Reason for Refusal for Japanese application No. 2021-572472 issued on Dec. 22, 2022.

(a)          (b)

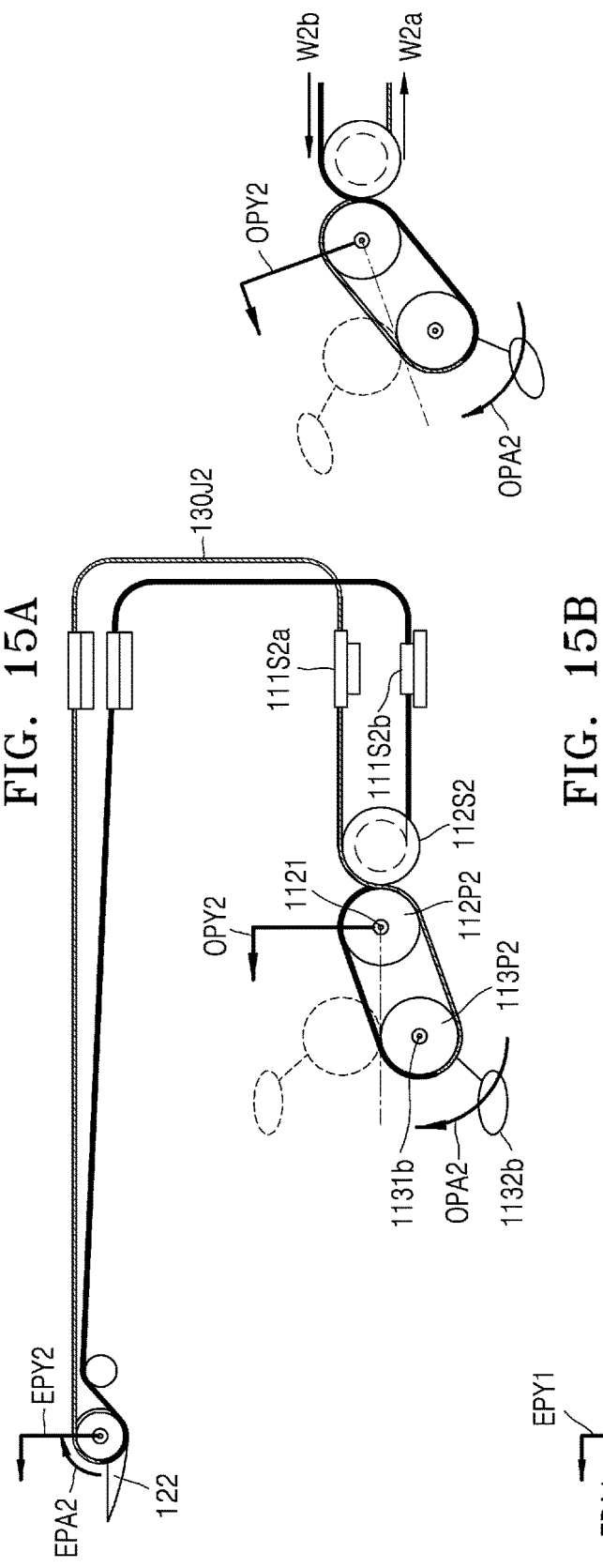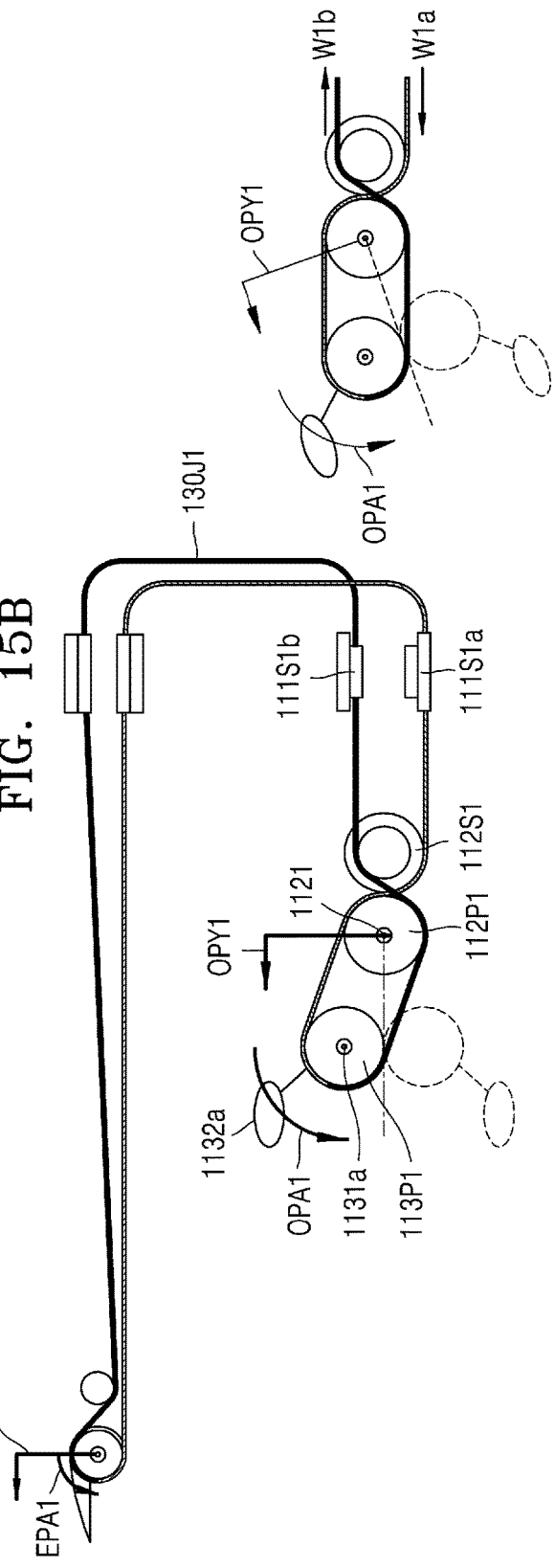

END TOOL OF SURGICAL INSTRUMENT AND SURGICAL INSTRUMENT INCLUDING THE SAME

CROSS-REFERENCE TO RELATED APPLICATIONS

This application is a continuation application of U.S. patent application Ser. No. 17/059,418 filed on Nov. 27, 2020, which is a national-stage under 35 USC 371 of PCT international application No. PCT/KR2019/014557 filed on Oct. 31, 2019, the entire disclosure of which is hereby incorporated by reference.

TECHNICAL FIELD

The present disclosure relates to an end tool of a surgical instrument and a surgical instrument having the same, and more particularly, to an end tool of a surgical instrument which may be manually operated in a laparoscopic surgery or other various surgeries and a surgical instrument having the same.

BACKGROUND ART

Medically, surgery refers to the treatment of a disease by using medical devices to cut, slit, or manipulate skin, mucous membrane, or other tissue. In particular, open surgery of cutting and opening the skin of a surgical site to treat, reshape, or remove organs therein causes bleeding, side effects, pain to the patient, and scars. Accordingly, recently, surgery using a robot or surgery performed by inserting only a medical device, for example, a laparoscope, a surgical instrument, a microsurgical microscope, or the like, in the body by forming a predetermined hole in the skin, has been spotlighted as an alternative.

A surgical instrument is a tool for performing surgery at a surgical site by manipulating an end tool provided at one end of a shaft passing through a hole drilled in the skin by a medical doctor using a predetermined driving unit or a robot arm. The end tool provided at the surgical instrument performs a rotation operation, a gripping operation, a cutting operation, or the like through a predetermined structure.

However, a surgical instrument according to the related art has a problem in that accessing a surgical site and performing various surgical motions are not easy because an end tool portion of the surgical instrument according to the related art is not bent. To address the above problem, surgical instruments having a bendable end tool portion have been developed. However, as a motion of a manipulating portion for bending an end tool or performing a surgical operation does not intuitively match with an actual motion of bending an end tool or performing a surgical treatment, from an operator's point of view, there is a problem in that an intuitive operation is not easy and it takes a long time to master a use method.

The above-mentioned background technology is technical information acquired by the inventor to derive the present invention or during the derivation process of the present invention, and is not necessarily a known technology disclosed to the general public before filing the present invention.

DESCRIPTION OF EMBODIMENTS

Technical Problem

Provided is a surgical instrument in which an actual motion of bending an end tool or performing a surgical treatment intuitively matches a motion of a manipulation portion corresponding thereto. In detail, to this end, provided are an end tool having various degrees of freedom, a manipulation portion having a structure to enable intuitive manipulation of a motion of the end tool, and a driving force transmission portion for transmitting a driving force of the manipulation portion to the end tool so that the end tool operates as manipulated by the manipulation portion.

Solution to Problem

According to an embodiment of the present disclosure, an end tool of a surgical instrument includes a first jaw and a second jaw capable of rotating independently of each other, a J11 pulley coupled to the first jaw and formed to be capable of rotating around a first axis, a J21 pulley coupled to the second jaw and formed to be capable of rotating around an axis that is substantially the same as or parallel to the first axis, an end tool hub including a pair of jaw pulley coupling portions formed to face each other and a guide portion connecting the pair of jaw pulley coupling portions, wherein at least parts of the J11 pulley and the J21 pulley are accommodated in a space formed by the pair of jaw pulley coupling portion and the guide portion, and a region adjacent to the J11 pulley and the J21 pulleys in the guide portion has a section that is curved with a certain radius of curvature, a J12 pulley and a J14 pulley formed at one side of the end tool hub to be capable of rotating around a second axis forming an angle with respect to the first axis, and a J22 pulley and a J24 pulley formed at one side of the end tool hub to be capable of rotating around an axis that is substantially the same as or parallel to the second axis.

According to another embodiment of the present disclosure, a surgical instrument includes an end tool formed to be capable of rotating in two or more directions and including a first jaw and a second jaw, each being formed to be rotatable, a manipulation portion configured to control a rotation of the end tool in the two or more directions, a driving force transmission portion including a first jaw wire connected to the manipulation portion and transmitting a rotation of the manipulation portion to the first jaw and a second jaw wire connected to the manipulation portion and transmitting a rotation of the manipulation portion to the second jaw, and a connection portion extending in a first direction (an X-axis), having one end portion to which the end tool is coupled and another end portion to which the manipulation portion is coupled to connect the manipulation portion and the end tool, and including a bent portion that is bent one or more times while connecting the end tool to the manipulation portion, wherein the end tool further includes a pair of jaw pulley coupling portions formed to face each other, and an end tool hub including a guide portion connecting the pair of jaw pulley coupling portions, and at least parts of the J11 pulley and the J21 pulley are accommodated in a space formed by the pair of jaw pulley coupling portion and the guide portion, and a region adjacent to the J11 pulley and the J21 pulleys in the guide portion has a section that is curved with a certain radius of curvature.

Other aspects, features, and advantages than those described above will become apparent from the following drawings, claims, and detailed description of the disclosure.

Advantageous Effects of Disclosure

According to the present disclosure, as a manipulating direction of a manipulation portion by a surgical operator and an operating direction of an end tool are intuitively the same direction, convenience of a surgical operator may be improved and accuracy, reliability, and rapidity of surgery may be improved.

BRIEF DESCRIPTION OF DRAWINGS

FIGS. 15A and 15B schematically illustrate a configuration of pulleys and wires related to an actuation motion and a yaw motion of the surgical instrument of FIG. 12 according to an embodiment of the disclosure, for a first jaw and a second jaw.

BEST MODE

Figure 1A:
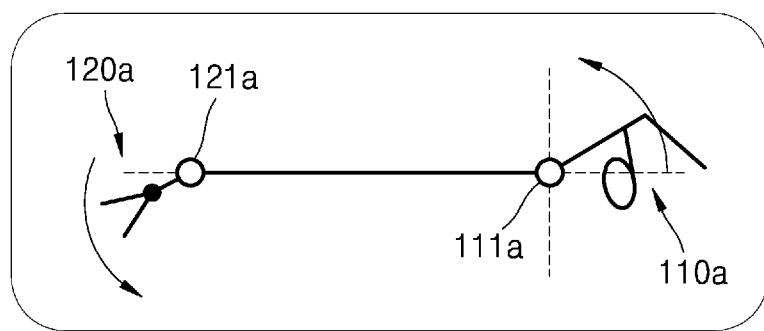
FIG. 1A is a conceptual view of a pitch motion of a surgical instrument according to the related art.

As the disclosure allows for various changes and numerous embodiments, embodiments will be illustrated in the drawings and described in detail in the written description. However, this is not intended to limit the disclosure to particular modes of practice, and it is to be appreciated that all changes, equivalents, and substitutes that do not depart from the spirit and technical scope of the disclosure are encompassed in the disclosure. In the description of the disclosure, certain detailed explanations of the related art are omitted when it is deemed that they may unnecessarily obscure the essence of the disclosure.

While such terms as "first," "second," etc., may be used to describe various components, such components must not be limited to the above terms. The above terms are used only to distinguish one component from another.

The terms used in the specification are merely used to describe embodiments, and are not intended to limit the disclosure. An expression used in the singular encompasses the expression of the plural, unless it has a clearly different meaning in the context. In the specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, exemplary embodiments will be described in detail with reference to the accompanying drawings, and in the description with reference to the drawings, the same or corresponding constituents are indicated by the same reference numerals and redundant descriptions thereof are omitted.

Furthermore, in the description of various embodiments of the disclosure, it is not necessary to independently interpreted or worked each embodiment, and technical concepts described in the respective embodiments should be understood to be interpreted or worked by being combined to another embodiment that is individually described.

Surgical Instrument According to an Embodiment

A surgical instrument according to the present disclosure is characteristic in that, when a manipulation portion is rotated in any one direction with respect to at least one of pitch, yaw, and actuation motions, an end tool is rotated in the intuitively same direction as a manipulating direction of the manipulation portion.

Figure 1B:
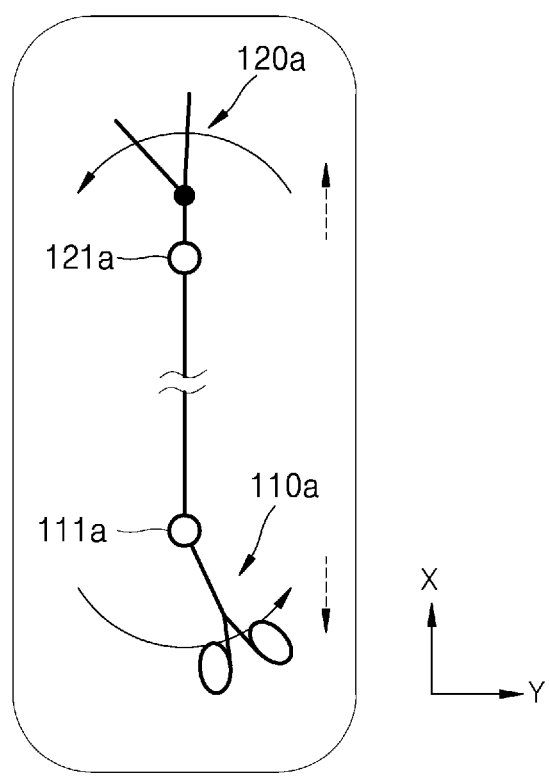
FIG. 1B is a conceptual view of a yaw motion thereof.

FIG. 1A is a concept view of a pitch motion of a surgical instrument according to the related art, and FIG. 1B is a concept view of a yaw motion thereof.

Referring to FIG. 1A, in performing a pitch motion of a surgical instrument according to the related art, in a state in which an end tool 120a is formed in front of a rotation center 121a of the end tool 120a, and a manipulation portion 110a is formed at the rear of a rotation center 111a of the manipulation portion 110a, when the manipulation portion 110a is rotated clockwise, the end tool 120a is also rotated clockwise, and when the manipulation portion 110a is rotated counterclockwise, the end tool 120a is also rotated counterclockwise. Referring to FIG. 1B, in performing a yaw motion of the surgical instrument according to the related art, in a state in which the end tool 120a is formed in front of the rotation center 121a of the end tool 120a, and the manipulation portion 110a is formed at the rear of the rotation center 111a of the manipulation portion 110a, when the manipulation portion 110a is rotated clockwise, the end tool 120a is also rotated clockwise, and when the manipulation portion 110a is rotated counterclockwise, the end tool 120a is also rotated counterclockwise. In this case, in view of the left and right directions of a user, when the user moves the manipulation portion 110a to the left, the end tool 120a moves to the right, and when the user moves the manipulation portion 110a to the right, the end tool 120a moves to the left. Consequently, as the user's manipulating direction and the end tool's operating direction are opposite to each other, the user may make an error and user's manipulation may not be easy.

Figure 1C:
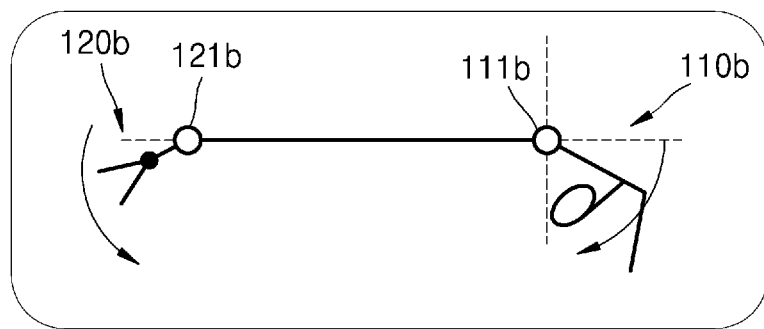
FIG. 1C is a conceptual view of a pitch motion of a surgical instrument according to another related art.
Figure 1D:
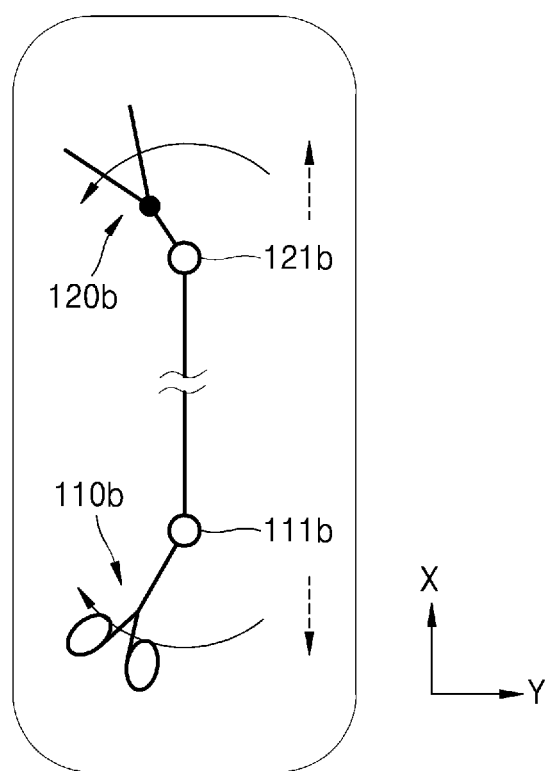
FIG. 1D is a conceptual view of a yaw motion thereof.

FIG. 1C is a concept view of a pitch motion of a surgical instrument according to another related art, FIG. 1D is a concept view of a yaw motion thereof.

Figure 1E:
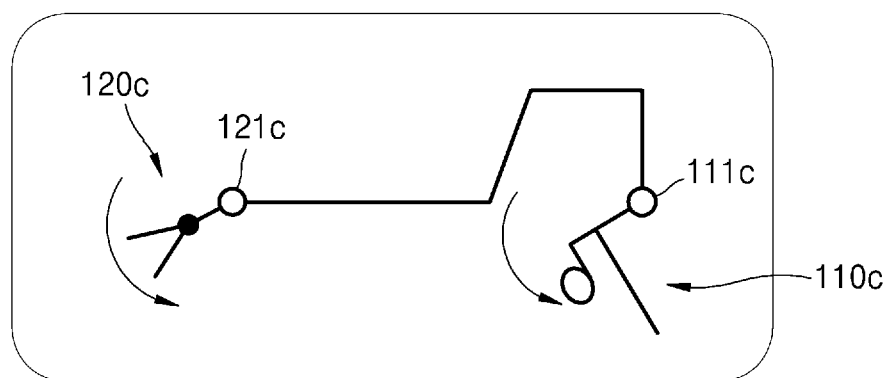
FIG. 1E is a conceptual view of a pitch motion of a surgical instrument according to the present disclosure.
Figure 1F:
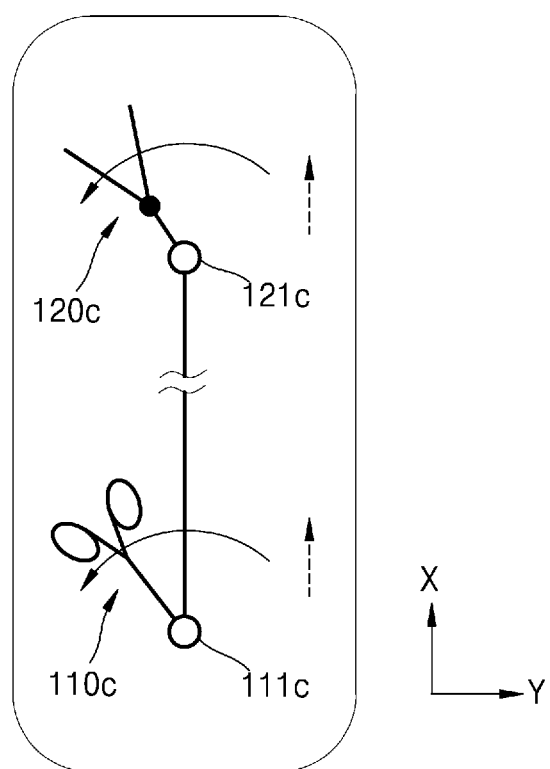
FIG. 1F is a conceptual view of a yaw motion thereof.

Referring to FIG. 1C, in a surgical instrument according to the related art, which is partially formed in a mirror symmetry, in performing a pitch motion, in a state in which an end tool 120*b* is formed in front of a rotation center 121*b* of the end tool 120*b*, and a manipulation portion 110*b* is formed at the rear of a rotation center 111*b* of the manipulation portion 110*b*, when the manipulation portion 110*b* is rotated clockwise, the end tool 120*b* is rotated counterclockwise, and when the manipulation portion 110*b* is rotated counterclockwise, the end tool 120*b* is rotated clockwise. In this case, in view of rotating directions of the manipulation portion 110*b* and the end tool 120*b*, a rotating direction in which the user rotates the manipulation portion 110*b* and a rotating direction of the end tool 120*b* according thereto are opposite to each other. Consequently, the user may be confused with the manipulating direction, and as the operation of a joint is not intuitive, the user may make an error. Furthermore, referring to FIG. 1D, in performing a yaw motion, in a state in which the end tool 120*b* is formed in front of the rotation center 121*b* of the end tool 120*b*, and the manipulation portion 110*b* is formed at the rear of the rotation center 111*b* of the manipulation portion 110*b*, when the manipulation portion 110*b* is rotated clockwise, the end tool 120*b* is rotated counterclockwise, and when the manipulation portion 110*b* is rotated counterclockwise, the end tool 120*b* is rotated clockwise. In this case, in view of rotating directions of the manipulation portion 110*b* and the end tool 120*b*, a rotating direction in which the user rotates the manipulation portion 110*b* and a rotating direction of the end tool 120*b* according thereto are opposite to each other. Consequently, the user may be confused with the manipulating direction, and as the operation of a joint is not intuitive, the user may make an error. In the user's pitch or yaw manipulation of the surgical instrument according to the related art, the user's manipulating direction and the end tool's operating direction do not match each other in view of one of the rotating direction and the left and right directions. This is because the configurations of the end tool and the manipulation portion are different from each other in the joint configuration of the surgical instrument according to the related art. In other words, while the end tool is formed in front of the rotation center of the end tool, the manipulation portion is formed at the rear of the rotation center of the manipulation portion. To address the above problem, a surgical instrument of FIGS. 1E and 1F according to an embodiment of the disclosure is characteristic in that an end tool 120*c* is formed in front of a rotation center 121*c* of the end tool 120*c* and a manipulation portion 110*c* is also formed in front of a rotation center 111*c* of the manipulation portion 110*c* so that the operations of the manipulation portion 110*c* and the end tool 120*c* are intuitively matched with each other. When the characteristics are expressed in a different way, unlike an existing example in which the manipulation portion 110*c* is close to the user with respect to a joint thereof (that is, away from the end tool 120*c*), as illustrated in FIGS. 1A, 1B, 1C, and 1D, the surgical instrument of FIGS. 1E and 1F according to an embodiment of the disclosure is formed such that at least a part of the manipulation portion 110*c* is closer to the end tool 120*c* with respect to a joint thereof (than the joint thereof) end tool at any one moment or more in a manipulation process.

In other words, in the surgical instrument according to the related art as illustrated in FIGS. 1A, 1B, 1C, and 1D, while the end tool is located in front of a rotation center thereof, the manipulation portion is formed at the rear of a rotation center thereof, and as the end tool is moved at a front side thereof with a rear side fixed through a motion of the manipulation portion that moves at a rear side thereof with a front side thereof fixed, it is not an intuitively matching structure. Accordingly, a mismatch occurs between the manipulation of the manipulation portion and the motion of the end tool in view of the left and right directions or in view of the rotating direction, which may confuse the user, and also as it is difficult to intuitively quickly perform the manipulation of the manipulation portion, an error may be made. In contrast, in the surgical instrument according to an embodiment of the disclosure, as both of the end tool and the manipulation portion are moved with respect to the rotation center formed at the rear side thereof, it may be said that the motions are intuitively matched with each other in terms of structure. In other words, as a moving part of the end tool is moved with respect to the rotation center formed at the rear side thereof, a moving part of the manipulation portion is also moved with respect to the rotation center formed at the rear side thereof, and thus it may be said that the motions are intuitively matched with each other in terms of structure. Accordingly, the user may intuitively quickly perform a control in a direction toward the end tool, and a possibility of making an error may be remarkably reduced. In the following description, a detailed mechanism enabling the above-described function is described below.

Figure 2:
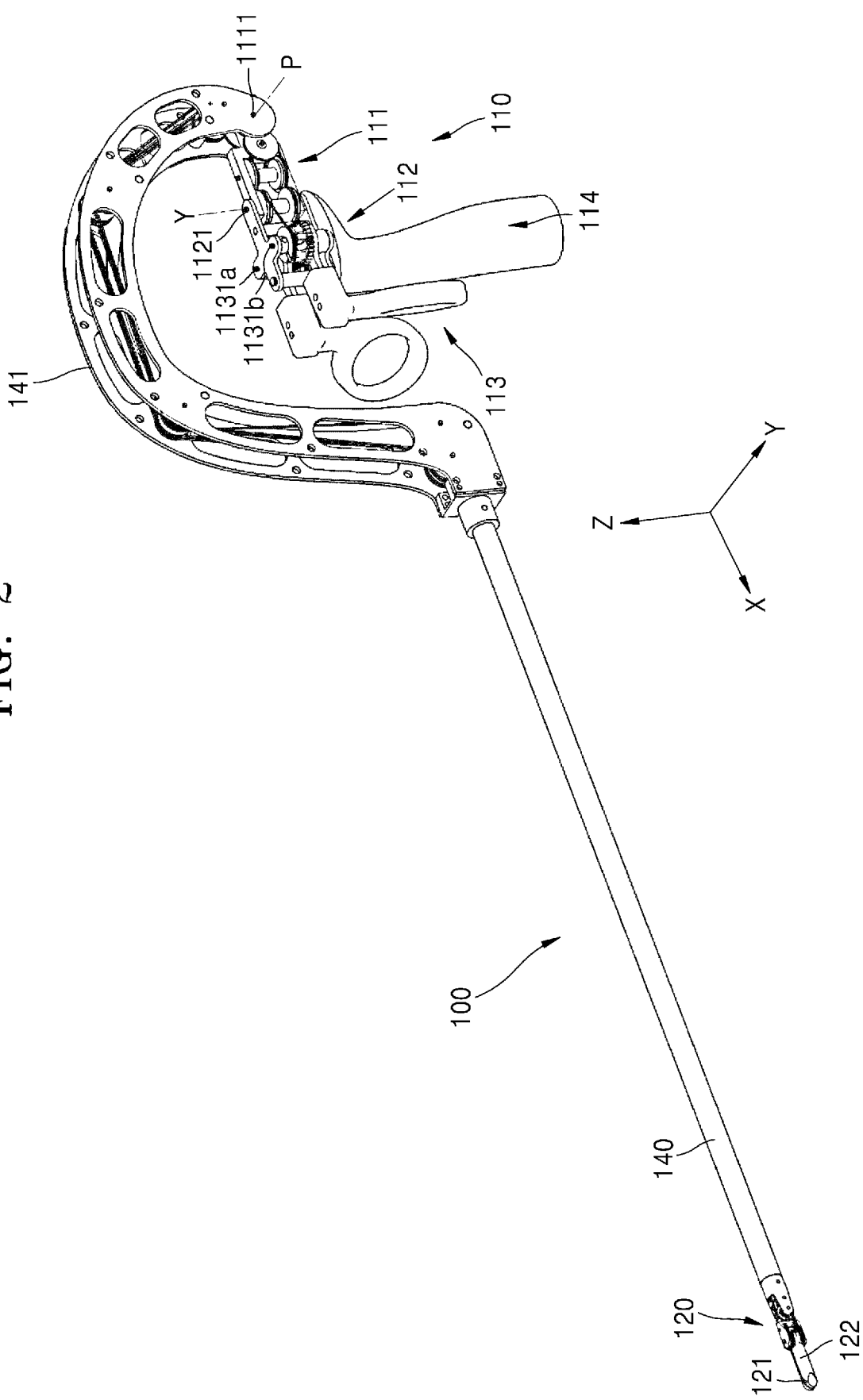
FIG. 2 is a perspective view of a surgical instrument according to an embodiment of the disclosure.
Figure 3:
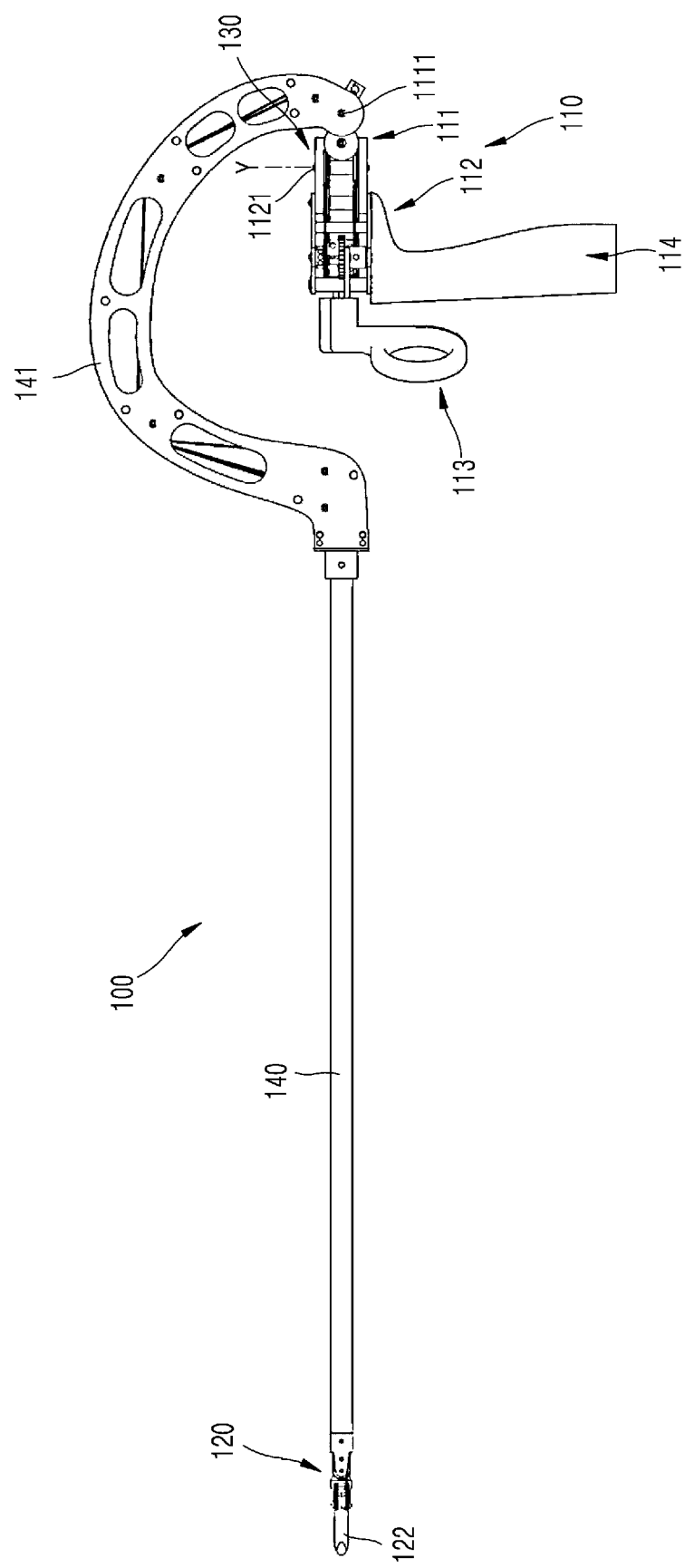
FIG. 3 is a side view of the surgical instrument of FIG. 2

FIG. 2 is a perspective view of a surgical instrument according to an embodiment of the disclosure, and FIG. 3 is a side view of the surgical instrument of FIG. 2.

Referring to FIGS. 2 and 3, a surgical instrument 100 according to an embodiment of the disclosure may include a manipulation portion 110, an end tool 120, a driving force transmission portion 130, and a connection portion 140. The connection portion 140 has a hollow shaft shape for accommodating therein one or more wires that are described below, one end portion to which the manipulation portion 110 is coupled, and the other end portion to which the end tool 120 is coupled, and may connect the manipulation portion 110 to the end tool 120. The connection portion 140 of the surgical instrument 100 according to an embodiment of the disclosure may characteristically include a bent portion 141 formed at the side of the manipulation portion 110. As such, as the end portion the connection portion 140 at the side of the manipulation portion 110 is formed to be bent, a pitch manipulation portion 111, a yaw manipulation portion 112, and an actuation manipulation portion 113 may be formed along an extension line of the end tool 120 or adjacent to the extension line. In other words, it may be said that the pitch manipulation portion 111 and the yaw manipulation portion 112 are at least partially accommodated in a concave portion formed by the bent portion 141. Due to the above-described shape of the bent portion 141, the shapes and motions of the manipulation portion 110 and the end tool 120 may be further intuitively matched with each other.

A plane on which the bent portion 141 is formed may be substantially the same plane as a pitch plane, that is, an X-Z plane of FIG. 2. As such, as the bent portion 141 is formed on substantially the same plane as the X-Z plane, interference with the manipulation portion 110 may be reduced. For intuitive motions of the end tool 120 and the manipulation portion 110, any form other than the X-Z plane may be possible.

The manipulation portion 110 is formed at the one end portion of the connection portion 140 and provided as an interface to be directly controlled by a medical doctor, for example, a tongs shape, a stick shape, a lever shape, or the like. When the medical doctor controls the manipulation portion 110, the end tool 120 that is connected to the interface and inserted into the body of a patient performs a certain motion, thereby performing surgery. Although FIG. 2 illustrates that the manipulation portion 110 is formed in a handle shape that is rotatable with fingered inserted therein, the concept of the present disclosure is not limited thereto, and various types of manipulation portions that are connected to the end tool 120 to manipulate the end tool 120 may be possible.

The end tool 120 is formed on the other end portion of the connection portion 140, and performs necessary motions for surgery by being inserted into a surgical site. As an example of the end tool 120, as illustrated in FIG. 2, a pair of jaws 121 and 122 for performing a grip motion may be used. However, the concept of the present disclosure is not limited thereto, and various devices for surgery may be used as the end tool 120. For example, a configuration of a cantilever cautery may be used as the end tool 120. The end tool 120 configured as above is connected to the manipulation portion 110 by the driving force transmission portion 130, and receives a driving force of the manipulation portion 110 through the driving force transmission portion 130 to perform a motion necessary for surgery, such as gripping, cutting, suturing, or the like.

The end tool 120 of the surgical instrument 100 according to an embodiment of the disclosure is formed to be capable of rotating in at least two directions, for example, the end tool 120 may perform a pitch motion around the Y-axis of FIG. 2 and simultaneously perform a yaw motion and an actuation motion around the Z-axis of FIG. 2.

The pitch, yaw, and actuation motions used in the present disclosure each are defined as follows.

First, the pitch motion means a motion of the end tool 120 rotating in a vertical direction with respect to the extension direction of the connection portion 140 (the X-axis direction of FIG. 2), that is, a rotating motion around the Y-axis of FIG. 2. In other words, the pitch motion means a motion of the end tool 120, which extends from the connection portion 140 in the extension direction of the connection portion 140 (the X-axis direction of FIG. 2), rotating vertically around the Y-axis with respect to the connection portion 140. Next, the yaw motion means a motion of the end tool 120 rotating in the left and right directions, that is, the Z-axis of FIG. 2, with respect to the extension direction of the connection portion 140 (the X-axis direction of FIG. 2). In other words, the yaw motion means a motion of the end tool 120, which extends from the connection portion 140 in the extension direction of the connection portion 140 (the X-axis direction of FIG. 2), rotating horizontally around the Z-axis with respect to the connection portion 140. In other words, the yaw motion means a motion of the two jaws 121 and 122 formed on the end tool 120 rotating around the Z-axis in the same direction. The actuation motion may mean a motion of the end tool 120 rotating around the same rotation axis as that of the yaw motion, while the two jaws 121 and 122 rotating in the opposite directions so as to be closed or opened. In other words, the actuation motion means a rotating motion of the two jaws 121 and 122 formed on the end tool 120 in the opposite directions around the Z-axis.

The driving force transmission portion 130 may connect the manipulation portion 110 to the end tool 120, transmit the driving force of the manipulation portion 110 to the end tool 120, and include a plurality of wires, pulleys, links, sections, gears, or the like. In the surgical instrument 100 according to an embodiment of the disclosure, the driving force transmission portion 130 may include a pitch wire 130P, a first jaw wire 130J1, and a second jaw wire 130J2.

In the following description, the manipulation portion 110, the end tool 120, the driving force transmission portion 130, and the like of the surgical instrument 100 of FIG. 2 are described in detail.

(End Tool)

Figure 4:
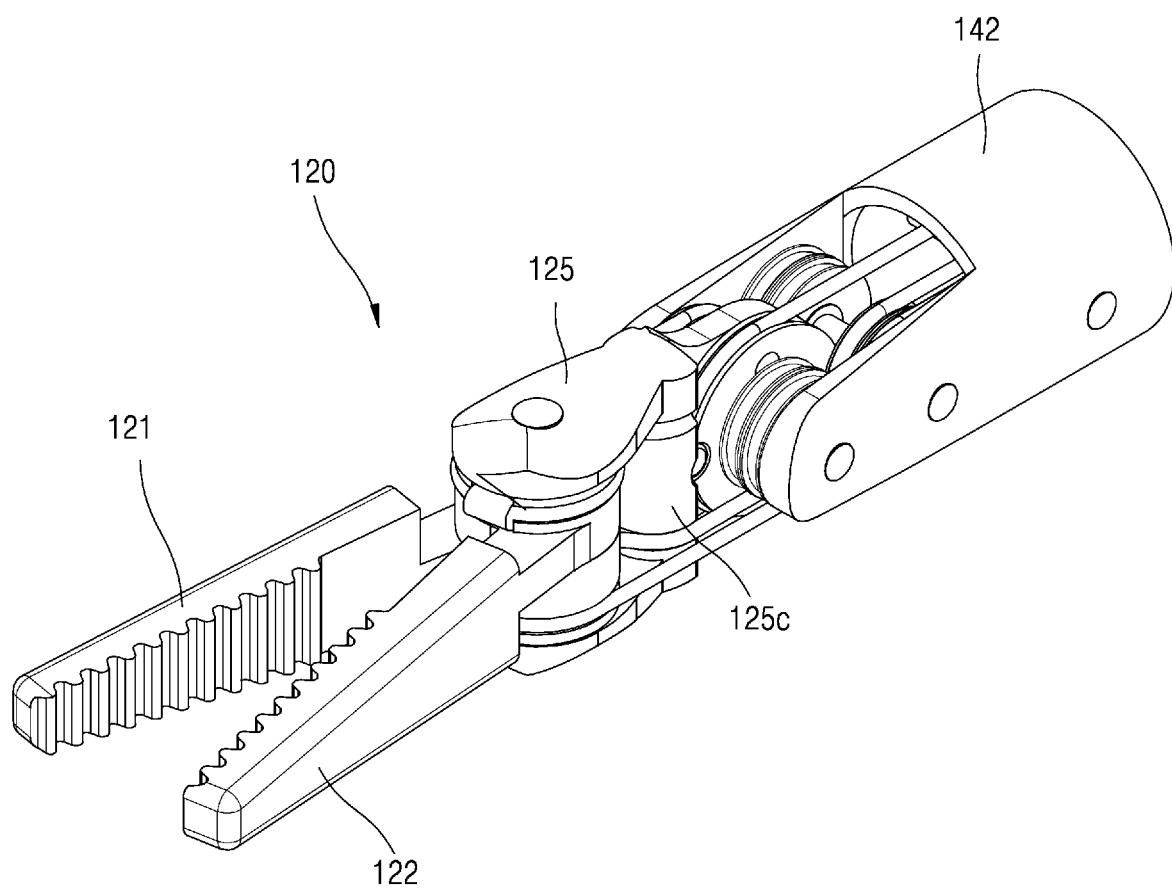
FIGS. 4 and 5 are perspective views of an end tool of the surgical instrument of FIG. 2.
Figure 5:
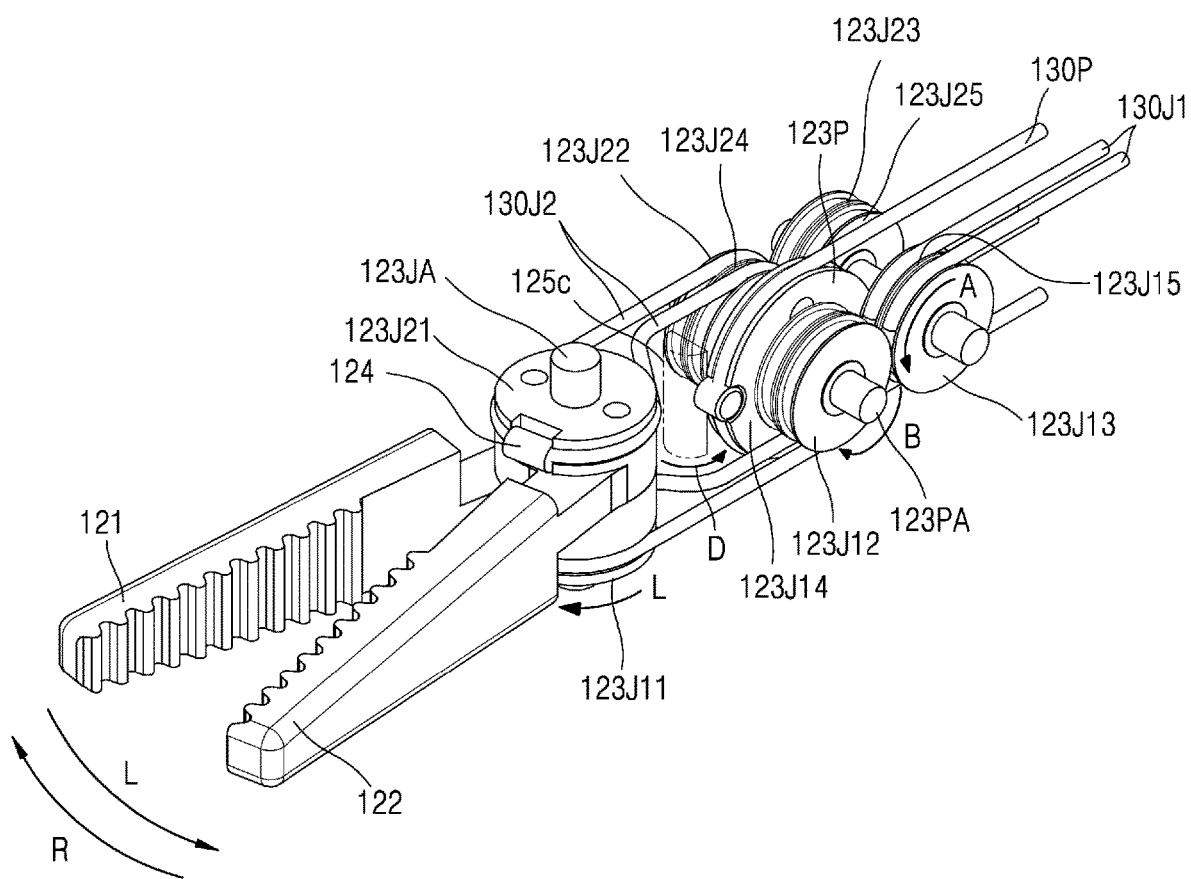
Figure 6:
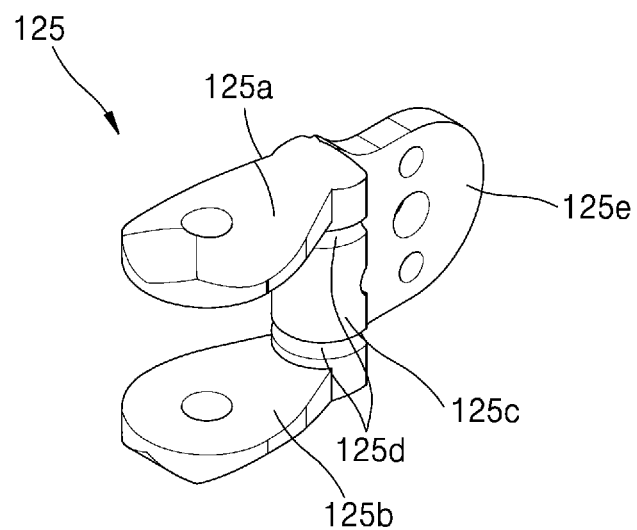
FIG. 6 illustrates an end tool hub of the surgical instrument of FIG. 4.
Figure 7:
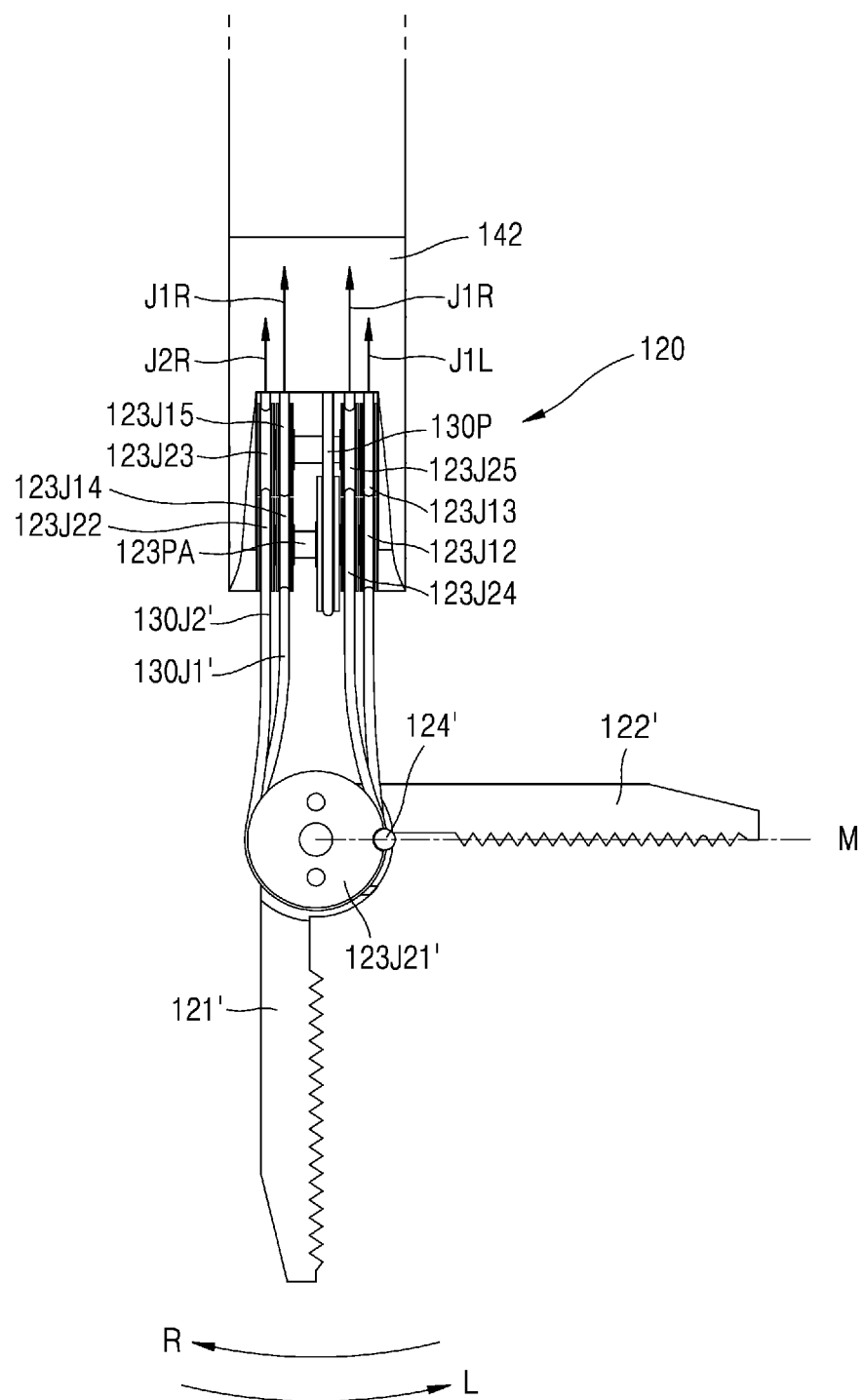
FIGS. 7 and 8 are plan views of an end tool of a surgical instrument according to the related art.
Figure 8:
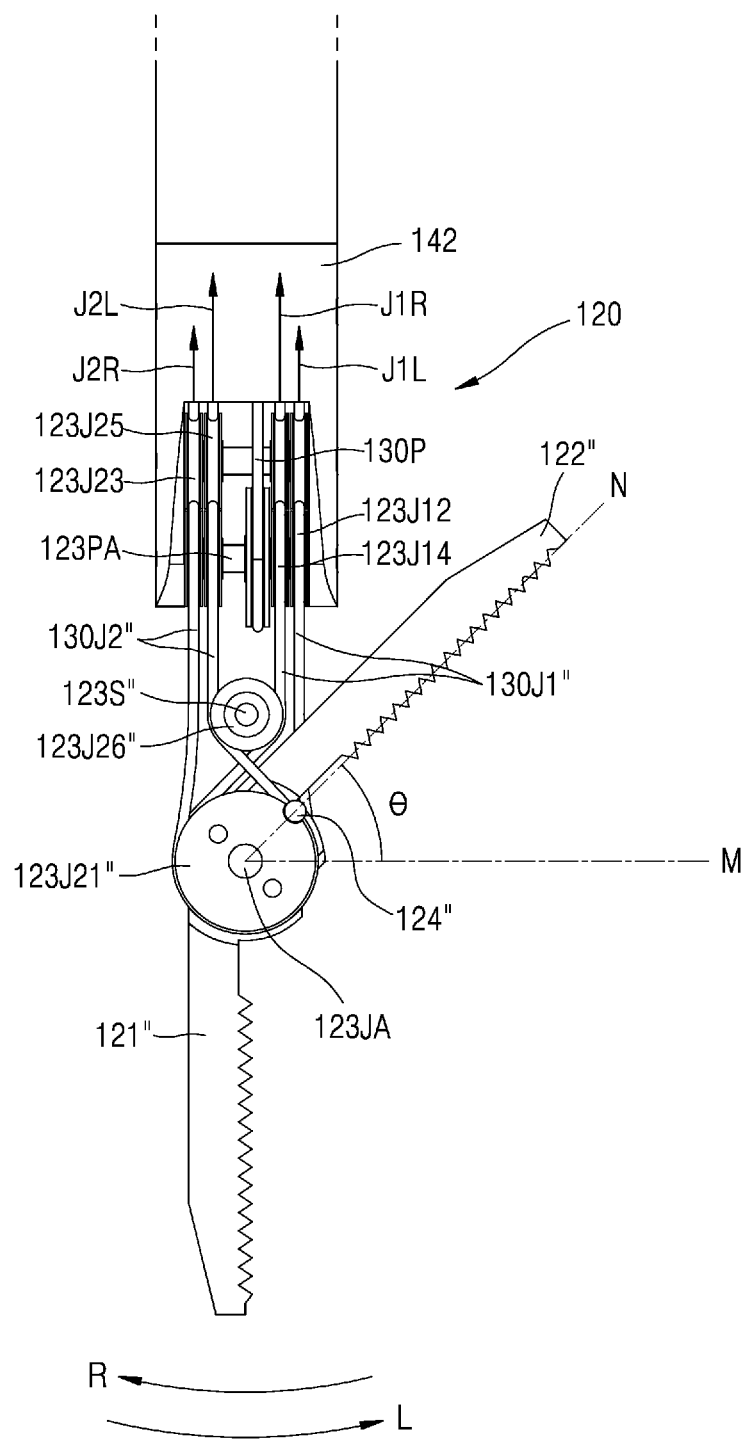
Figure 9:
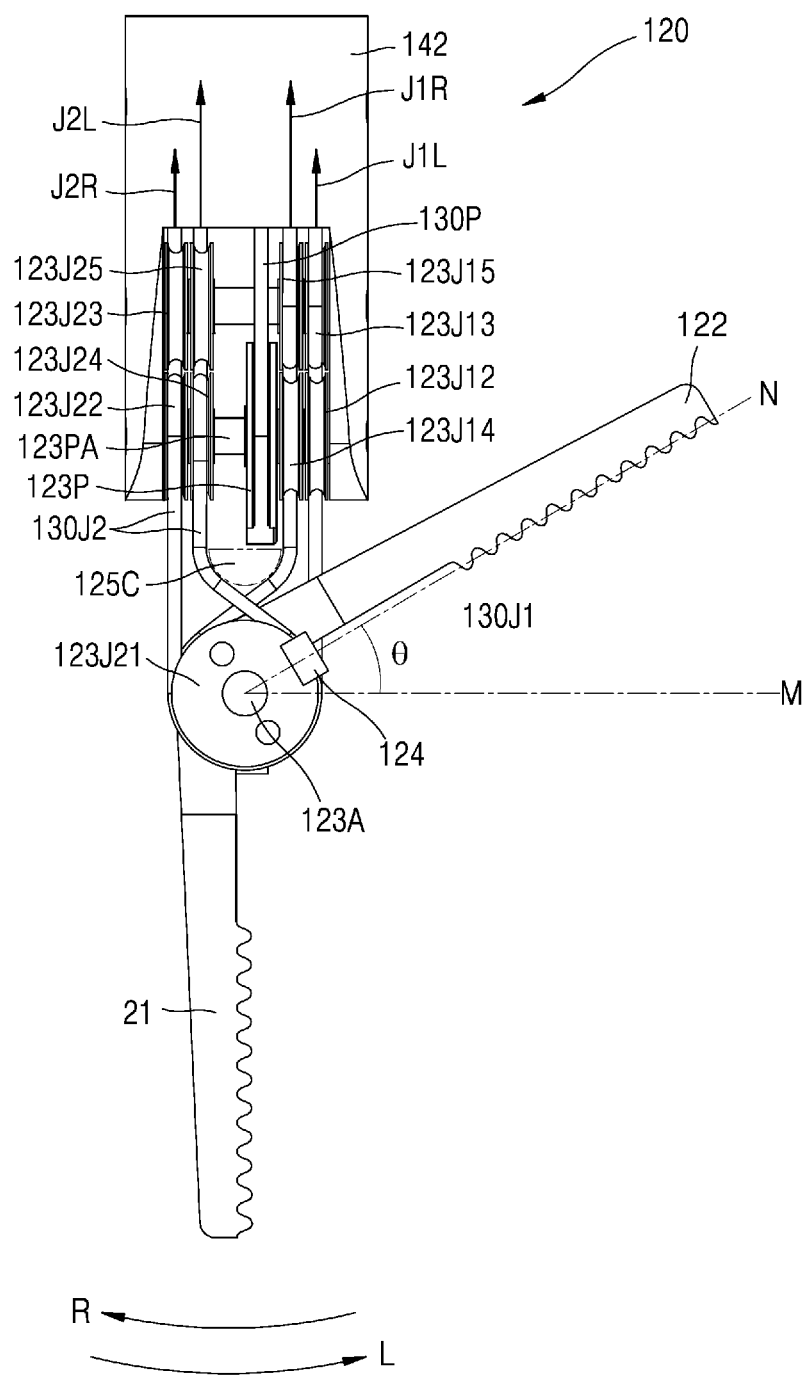
FIG. 9 is a plan view of the end tool of the surgical instrument of FIG. 2.
Figure 10:
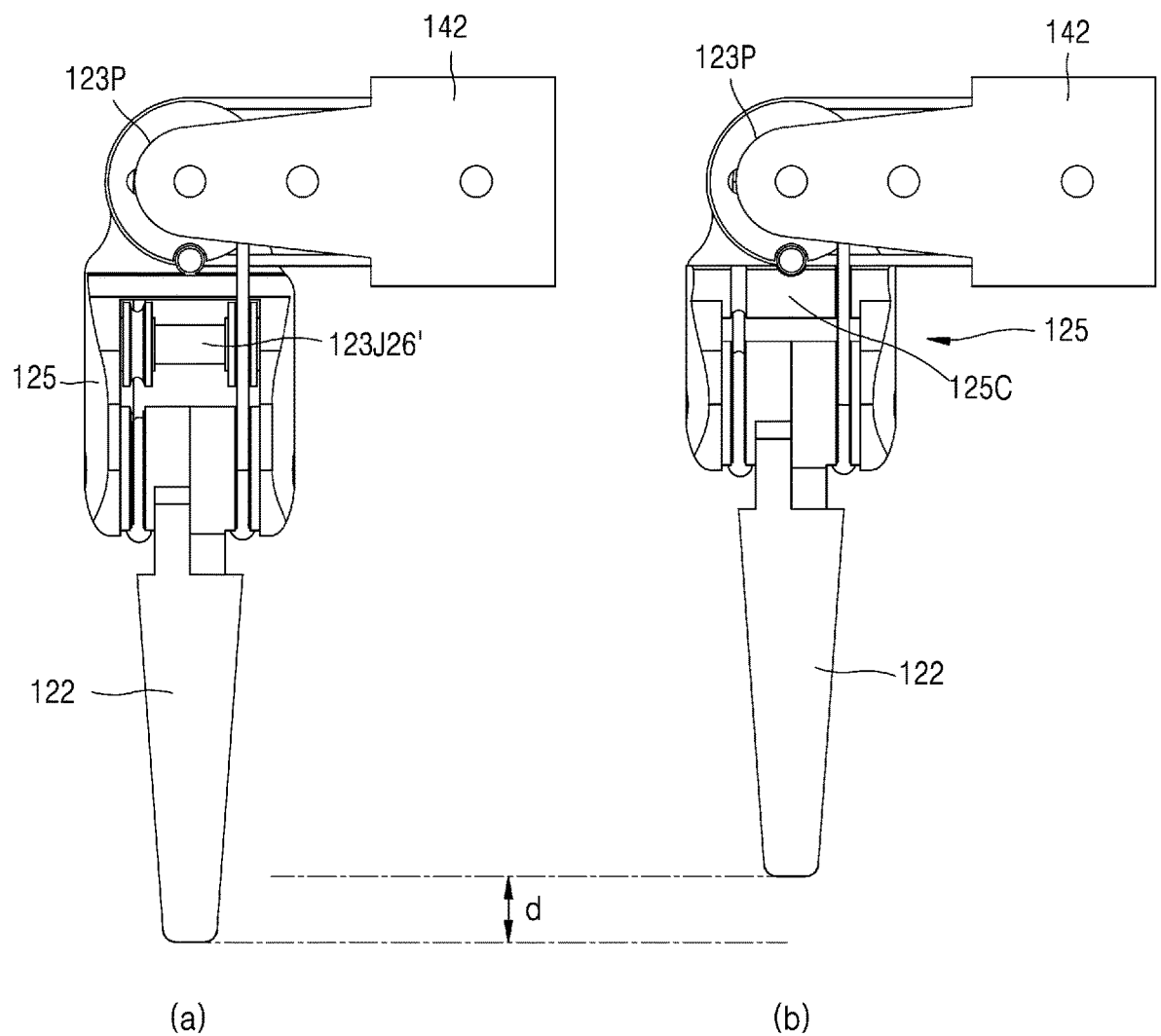
FIG. 10 illustrates a comparison between the end tool of the surgical instrument of FIG. 8 according to the related art and the end tool of the surgical instrument of FIG. 4 according to an embodiment of the disclosure.
Figure 11:
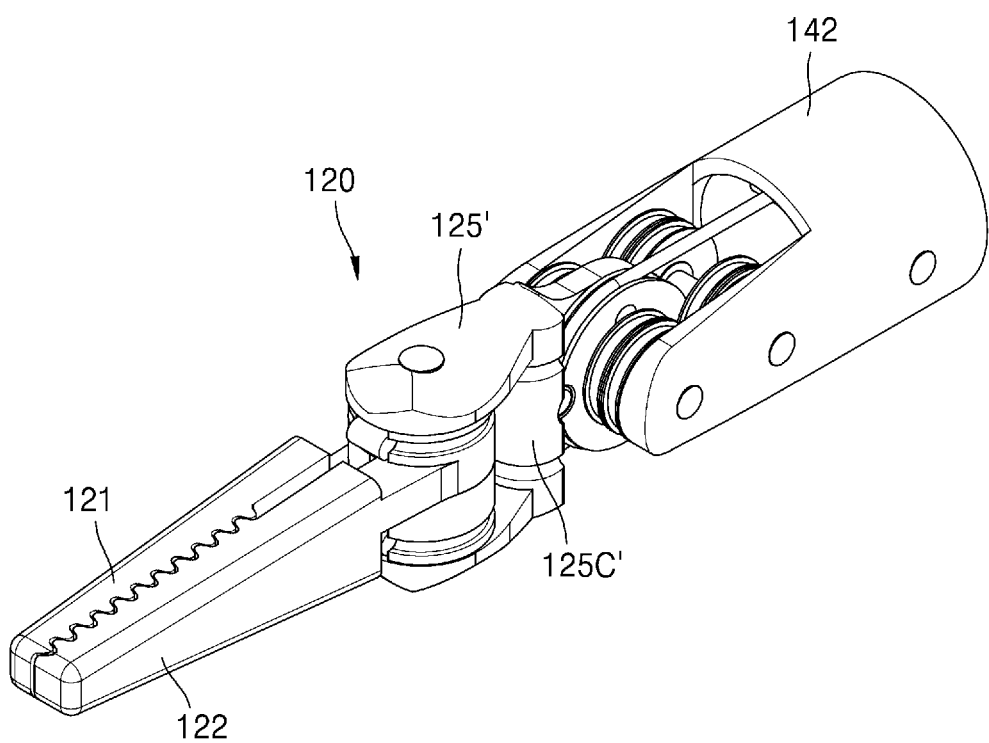
FIG. 11 illustrates a modified example of the end tool of FIG. 4.

FIGS. 4 and 5 are perspective views of an end tool of the surgical instrument of FIG. 2, and FIG. 6 illustrates an end tool hub of the surgical instrument of FIG. 4. FIGS. 7 and 8 are plan views of an end tool of a surgical instrument according to the related art, and FIG. 9 is a plan view of the end tool of the surgical instrument of FIG. 2. FIG. 10 illustrates a comparison between the end tool of the surgical instrument of FIG. 8 according to the related art and the end tool of the surgical instrument of FIG. 4 according to an embodiment of the disclosure, and FIG. 11 illustrates a modified example of the end tool of FIG. 4.

First, Referring to FIGS. 4, 5, 6, and 9, the end tool 120 according to an embodiment of the present disclosure may include the jaws 121 and 122 for performing a grip motion, that is, the first jaw 121 and the second jaw 122. Furthermore, the end tool 120 may include a J11 pulley 123J11, a J12 pulley 123J12, a J13 pulley 123J13, a J14 pulley 123J14, and a J15 pulley 123J15, which are related to a rotating motion of the first jaw 121, and a J21 pulley 123J21, a J22 pulley 123J22, a J23 pulley 123J23, a J24 pulley 123J24, and a J25 pulley 123J25, which are related to a rotating motion of the second jaw 122. The first jaw 121, the J11 pulley 123J11, the J12 pulley 123J12, the J14 pulley 123J14, the second jaw 122, the J21 pulley 123J21, the J22 pulley 123J22, and the J24 pulley 123J24 all may be formed to rotate together around an end tool pitch rotation shaft 123PA.

A connection portion hub 142 is formed on the one end portion of the connection portion 140 that is coupled to the end tool 120. The J12 pulley 123J12, the J13 pulley 123J13, the J14 pulley 123J14, and the J15 pulley 123J15, and the J22 pulley 123J22, the J23 pulley 123J23, the J24 pulley 123J24, and the J25 pulley 123J25, are all coupled to the connection portion hub 142.

Although the pulleys facing each other are illustrated in the drawings formed parallel to each other, the concept of the present disclosure is not limited thereto, each of the pulleys may be variously formed at positions and in sizes suitable for a configuration of the end tool.

The J11 pulley 123J11 and the J21 pulley 123J21 are formed to face each other and independently rotate around a jaw rotation shaft 123JA. While the first jaw 121 is fixedly coupled to the J11 pulley 123J11 to rotate together with the J11 pulley 123J11, the second jaw 122 is fixedly coupled to the J21 pulley 123J21 to rotate together with the J21 pulley 123J21. The yaw motion and the actuation motion of the end tool 120 are performed according to the rotations of the J11 pulley 123J11 and the J21 pulley 123J21. In other words, when the J11 pulley 123J11 and the J21 pulley 123J21 rotate in the same direction, a yaw motion is performed, and when the J11 pulley 123J11 and the J21 pulley 123J21 rotate in the opposite direction, an actuation motion is performed.

The end tool 120 may further include a pitch pulley 123P around which the pitch wire 130P is wound. Furthermore, the end tool 120 may further include an end tool hub 125 that forms a base of the end tool 120 so that the J11 pulley 123J11, the J21 pulley 123J21, the pitch pulley 123P, or the like are coupled thereto.

An embodiment of the present disclosure has a feature that a guide portion 125c for performing a function as an auxiliary pulley is formed as the end tool hub 125. In other words, the guide portion 125c for guiding paths of the first jaw wire 130J1 and the second jaw wire 130J2 are formed on the end tool hub 125. The guide portion 125c may be disposed between the J11 pulley 123J11 and the J12 pulley 123J12/the J14 pulley 123J14. Furthermore, the guide portion 125c may be disposed between the J21 pulley 123J21 and the J22 pulley 123J22/the J24 pulley 123J24. The guide portion 125c of the end tool hub 125 may perform a function of a kind of auxiliary pulley to change a path of a wire. The guide portion 125c of the end tool hub 125, which performs a function of an auxiliary pulley, is described below in detail.

In the following description, constituent elements related to the rotation of the J11 pulley 123J11 are described.

The J12 pulley 123J12 and the J14 pulley 123J14 are disposed at one side of the J11 pulley 123J11 to face each other. The J12 pulley 123J12 and the J14 pulley 123J14 are formed to independently rotate around the end tool pitch rotation shaft 123PA. Furthermore, the J13 pulley 123J13 and the J15 pulley 123J15 are disposed respectively at one side of the J12 pulley 123J12 and the J14 pulley 123J14 (in the X-axis direction) to face each other. The J13 pulley 123J13 and the J15 pulley 123J15 are formed to independently rotate around the Y-axis direction. Although the J12 pulley 123J12, the J13 pulley 123J13, the J14 pulley 123J14, and the J15 pulley 123J15 are all illustrated to be rotatable around the Y-axis direction, the concept of the present disclosure is not limited thereto, and rotation-axes of the respective pulleys may be formed various directions suitable for a configuration thereof.

The J12 pulley 123J12 and the J14 pulley 123J14 are disposed at a first side (the right side of the pitch pulley 123P in FIG. 9) with respect to a plane perpendicular to the Y-axis and passing through a center-axis (X-axis) of the connection portion 140. This is because the guide portion 125c of the end tool hub 125 changes an arrangement path of the first jaw wire 130J1 by performing a function of an auxiliary pulley. Likewise, the J13 pulley 123J13 and the J15 pulley 123J15 are also disposed at the same side (first side) as the J12 pulley 123J12 and the J14 pulley 123J14.

Likewise, the J22 pulley 123J22 and the J24 pulley 123J24 are disposed at a second side (the left side of the pitch pulley 123P in FIG. 9) with respect to the plane perpendicular to the Y-axis and passing through the center-axis (X-axis) of the connection portion 140. This is because the guide portion 125c of the end tool hub 125 changes an arrangement path of the second jaw wire 130J2 by performing a function of an auxiliary pulley. Likewise, the J23 pulley 123J23 and the J25 pulley 123J25 are also disposed at the same side (second side) as the J22 pulley 123J22 and the J24 pulley 123J24.

The first jaw wire 130J1 is sequentially wound around the J13 pulley 123J13, the J12 pulley 123J12, the J11 pulley 123J11, the guide portion 125c of the end tool hub 125, the J14 pulley 123J14, and the J15 pulley 123J15 by at least partially contacting the same, and the first jaw wire 130J1 moves along the pulleys while rotating the pulleys.

In detail, the first jaw wire 130J1 extending from the connection portion 140 is first wound around the J13 pulley 123J13 in an arrow A direction of FIG. 5 (counterclockwise when viewed on the X-Z plane), and then wound around the J12 pulley 123J12 in an arrow B direction of FIG. 5 (clockwise when viewed on the X-Z plane). Then, the first jaw wire 130J1 is wound around the J11 pulley 123J11 in an arrow C direction of FIG. 5 (counterclockwise when viewed on the X-Y plane), and then wound around the guide portion 125c of the end tool hub 125 in an arrow D direction of FIG. 5 (clockwise when viewed on the X-Y plane). Then, the first jaw wire 130J1 is first wound around the J14 pulley 123J14 in a direction opposite to the arrow B direction of FIG. 5 (counterclockwise when viewed on the X-Z plane), and then wound around the J15 pulley 123J15 in a direction opposite to the arrow A direction of FIG. 5 (clockwise when viewed on the X-Z plane) and drawn into the connection portion 140.

Accordingly, when the first jaw wire 130J1 is pulled in a direction indicated by an arrow J1R of FIG. 9, the first jaw wire 130J1 rotates the J15 pulley 123J15, the J14 pulley 123J14, the J11 pulley 123J11, the J12 pulley 123J12, and the J13 pulley 123J13. In this state, the J11 pulley 123J11 is rotated in an arrow R direction of FIG. 9 to rotate the first jaw 121 together.

Reversely, when the first jaw wire 130J1 is pulled in a direction indicated by an arrow J1L of FIG. 9, the first jaw wire 130J1 rotates the J13 pulley 123J13, the J12 pulley 123J12, the J11 pulley 123J11, the J14 pulley 123J14, and the J15 pulley 123J15. In this state, the J11 pulley 123J11 is rotated in an arrow L direction of FIG. 9 to rotate the first jaw 121 together.

Next, constituent elements related to the rotation of the J21 pulley 123J21 are described.

The J22 pulley 123J22 and the J24 pulley 123J24 are disposed at one side of the J21 pulley 123J21 to face each other. The J22 pulley 123J22 and the J24 pulley 123J24 are formed to independently rotate around the end tool pitch rotation shaft 123PA. Furthermore, the J23 pulley 123J23 and the J25 pulley 123J25 are disposed respectively at one side of the J22 pulley 123J22 and the J24 pulley 123J24 (in the X-axis direction) to face each other. The J23 pulley 123J23 and the J25 pulley 123J25 are formed to independently rotate around the Y-axis direction. Although the J22 pulley 123J22, the J23 pulley 123J23, the J24 pulley 123J24, and the J25 pulley 123J25 are all illustrated to be rotatable around the Y-axis direction, the concept of the present disclosure is not limited thereto, and rotation-axes of the respective pulleys may be formed in various directions suitable for a configuration thereof.

A second jaw wire 130J2 is sequentially wound around the J23 pulley 123J23, the J22 pulley 123J22, the J21 pulley 123J21, the guide portion 125c of the end tool hub 125, the J24 pulley 123J24, and the J25 pulley 123J25 by at least partially contacting the same, and the second jaw wire 130J2 moves along the pulleys while rotating the pulleys.

Accordingly, when the second jaw wire 130J2 is pulled in a direction indicated by an arrow J2R of FIG. 9, the second jaw wire 130J2 rotates the J23 pulley 123J23, the J22 pulley 123J22, the J21 pulley 123J21, the J24 pulley 123J24, and the J25 pulley 123J25. In this state, the J21 pulley 123J21 is rotated in the arrow R direction of FIG. 9 to rotate the second jaw 122 together.

Reversely, when the second jaw wire 130J2 is pulled in a direction indicated by an arrow J2L of FIG. 9, the second jaw wire 130J2 rotates the J25 pulley 123J25, the J24 pulley 123J24, the J21 pulley 123J21, the J22 pulley 123J22, and the J23 pulley 123J23. In this state, the J21 pulley 123J21 is rotated in the arrow L direction of FIG. 9 to rotate the second jaw 122 together.

When the one end portion of the first jaw wire 130J1 is pulled in a direction indicated by the arrow J1R of FIG. 9 and simultaneously the other end portion of the first jaw wire 130J1 is pulled in a direction indicated by the arrow J1L of FIG. 9 (that is, when both end portions of the first jaw wire 130J1 are pulled), as the first jaw wire 130J1 is wound around lower sides of the J12 pulley 123J12 and the J14 pulley 123J14 to be capable of rotating around the end tool pitch rotation shaft 123PA, as illustrated in FIG. 5, the J11 pulley 123J11 to which the first jaw wire 130J1 is fixedly coupled, the first jaw 121, the jaw rotation shaft 123JA, the end tool hub 125, and the second jaw 122 connected thereto are rotated counterclockwise together around the end tool pitch rotation shaft 123PA. Consequently, the end tool 120 is rotated downward, thereby performing a pitch motion. At this time, as the second jaw 122 and the second jaw wire 130J2 fixedly coupled thereto are wound around upper sides of the J22 pulley 123J22 and the J24 pulley 123J24 to be capable of rotating around the end tool pitch rotation shaft 123PA, both end portions of the second jaw wire 130J2 are moved in the opposite directions of the arrows J2L and J2R.

Reversely, when the one end portion of the second jaw wire 130J2 is pulled in a direction toward the arrow J2R of FIG. 9 and simultaneously the other end portion of the second jaw wire 130J2 is pulled in a direction toward the arrow J2L of FIG. 9, the second jaw wire 130J2 is wound around the upper sides of the J22 pulley 123J22 and the J24 pulley 123J24 to be capable of rotating around the end tool pitch rotation shaft 123PA, as illustrated in FIG. 5, the J21 pulley 123J21 to which the second jaw wire 130J2 is fixedly coupled, the second jaw 122, the jaw rotation shaft 123JA, the end tool hub 125, and the first jaw 121 connected thereto are rotated clockwise together around the end tool pitch rotation shaft 123PA. Consequently, the end tool 120 is rotated upward, thereby performing a pitch motion. At this time, as the first jaw wire 130J1 fixedly coupled to the first jaw 121 is wound around the lower sides of the J12 pulley 123J12 and the J14 pulley 123J14 to be capable of rotating around the end tool pitch rotation shaft 123PA, both end portions of the first jaw wire 130J1 are moved in a direction opposite to the arrows J1L and J1R.

In a surgical instrument 100 of the present disclosure, the end tool 120 may further include the pitch pulley 123P, the manipulation portion 110 may further include a pitch wire end pulley 115P, and the driving force transmission portion 130 may further include the pitch wire 130P. In detail, the pitch pulley 123P of the end tool 120 is rotatable around the end tool pitch rotation shaft 123PA and may be fixedly coupled to the end tool hub 125. A pitch wire end pulley 115P of the manipulation portion 110 is rotatable around a pitch rotation shaft (1111) and may be fixedly coupled to a pitch manipulation portion (not shown). Furthermore, the pitch wire 130P may connect the pitch pulley 123P of the end tool 120 to the pitch wire end pulley 115P of the manipulation portion 110.

Accordingly, while a user grips a first handle 114 of the manipulation portion 110 with a hand, when the first handle 114 is rotated around a pitch rotation shaft 1111, the pitch pulley coupled to the first handle 114 rotates around the pitch rotation shaft 1111, the rotation of the pitch pulley is transmitted to the pitch pulley 123P of the end tool 120 via the pitch wire 130P so that the pitch pulley 123P is rotated together. Consequently, the end tool 120 is rotated, thereby performing a pitch motion.

In other words, the surgical instrument 100 according to an embodiment of the disclosure, which includes the pitch pulley 123P of the end tool 120, the pitch wire end pulley 115P of the manipulation portion 110, and the pitch wire 130P of the driving force transmission portion 130, may more completely transmit a driving force of the pitch motion of the pitch manipulation portion 111 to the end tool 120, thereby improving motion reliability.

In the following description, the end tool hub 125 is described in detail, particularly the guide portion 125c of the end tool hub 125 performing a function of an auxiliary pulley, is mainly described.

The end tool hub 125 may include a pair of jaw pulley coupling portions 125a and 125b, the guide portion 125c, a guide groove 125d, and a pitch pulley coupling portion 125e.

In detail, the jaw pulley coupling portions 125a and 125b are formed to face each other, and the J11 pulley 123J11 and the J21 pulley 123J21 are accommodated therein. Furthermore, as a through hole is formed in each of the jaw pulley coupling portions 125a and 125b, the jaw rotation shaft 123JA penetrates the jaw pulley coupling portions 125a and 125b, the J11 pulley 123J11, and the J21 pulley 123J21 so as to couple the same.

The jaw pulley coupling portions 125a and 125b are connected by the guide portion 125c. In other words, the jaw pulley coupling portions 125a and 125b that are parallel to each other are coupled by the guide portion 125c that is roughly formed in a perpendicular direction, the jaw pulley coupling portions 125a and 125b and the guide portion 125c forms about a "π" shape, and the J11 pulley 123J11 and the J21 pulley 123J21 are accommodated therein.

In other words, it may be seen that the jaw pulley coupling portions 125a and 125b extends, in the X-axis direction, from both end portions of the guide portion 125c that is formed long in Z-axis direction.

The guide portion 125c may have a cylindrical shape having a roughly semi-circular section. The semi-circular portion may be dispose to protrude toward the J11 pulley 123J11 and the J21 pulley 123J21. In other words, it may be said that the guide portion 125c protrudes toward a space formed by the jaw pulley coupling portions 125a and 125b and the guide portion 125c. In other words, in the guide portion 125c, a region adjacent to the jaw pulley coupling portions 125a and 125b has a section that is curved with a certain radius of curvature.

Alternatively, in other words, the guide portion 125c, which is wound with the first jaw wire 130J1 and the second jaw wire 130J2, may guide the paths of the first jaw wire 130J1 and the second jaw wire 130J2, performing a function as a kind of pulley member. However, the guide portion 125c, which is not a member rotating around a certain axis like a pulley in a sense, may be fixedly formed as a part of the end tool hub 125, and may partially similarly perform a function of a pulley around which a wire is wound.

In the drawings, the guide portion 125c is illustrated to have a cylindrical shape with a section that is roughly semi-circular. In other words, at least a part of the section of the guide portion 125c on the X-Y plane forms a certain arc shape. However, the concept of the present disclosure is not limited thereto, and the section may have a certain radius of curvature like an oval or a parabola, or a corner of a polygonal column is rounded to a certain degree, so that the section may have various shapes and sizes suitable for guiding the paths of the first jaw wire 130J1 and the second jaw wire 130J2.

The guide groove 125d for guiding the paths of the first jaw wire 130J1 and the second jaw wire 130J2 well may be further formed in a portion of the guide portion 125c contacting the first jaw wire 130J1 and the second jaw wire 130J2. The guide groove 125d may have a groove shape recessed to a degree from a protruding surface of the guide portion 125c.

Although the guide groove 125d is illustrated in the drawings as being formed in the entire arc surface of the guide portion 125c, the concept of the present disclosure is not limited thereto, and the guide groove 125d may be formed only in a part of the arc surface of the guide portion 125c, as necessary.

As such, by further forming the guide groove 125d in the guide portion 125c, unnecessary friction between the first jaw wire 130J1 and the second jaw wire 130J2 is reduced so that durability of the wires may be improved.

The pitch pulley coupling portion 125e may be further formed on the guide portion 125c in a direction opposite to the direction in which the jaw pulley coupling portions 125a and 125b are formed. The pitch pulley coupling portion 125e may be formed in a direction parallel to the pitch pulley 123P, that is, on the X-Z plane. A through hole into which the end tool pitch rotation shaft 123PA is penetrated and inserted may be formed in the pitch pulley coupling portion 125e, and the end tool pitch rotation shaft 123PA penetrates the pitch pulley coupling portion 125e and the pitch pulley 123P so that the two members may be coupled to each other. The pitch pulley coupling portion 125e is formed deviated to a certain degree toward one side than the center thereof, when viewed on the X-Y plane, thereby forming balance overall when the pitch pulley 123P is coupled thereto.

In the following description, the role and function of the guide portion 125c are described in detail.

The guide portion 125c contacts the first jaw wire 130J1 and the second jaw wire 130J2 and changes the arrangement path of the first jaw wire 130J1 and the second jaw wire 130J2 to a certain degree, thereby increasing the rotational radius of each of the first jaw 121 and the second jaw 122.

In other words, when no auxiliary pulley is disposed as illustrated in FIG. 7, each of a first jaw 121' and a second jaw 122' may be rotated to a right angle only. In an embodiment of the disclosure, as the end tool hub 125 is further provided with the guide portion 125c, an effect of increasing the maximum rotation angle by θ as shown in FIG. 9 may be obtained. This enables a motion of the two jaws of the end tool 120 being opened for an actuation motion while the two jaws are yaw-rotated by 90° in the arrow L direction. This is because the second jaw 122 is rotated by an additional angle θ as illustrated in FIG. 9. Likewise, an actuation motion is possible even when the two jaws are yaw-rotated in the arrow R direction. In other words, a feature of increasing the range of yaw rotation in which an actuation motion is possible may be obtained through the configuration of the guide portion 125c of the end tool hub 125. Furthermore, by forming the guide portion 125c on the end tool hub 125 that already exists, without adding a separate structure such as an auxiliary pulley, a feature of increasing the range of rotation without adding a component and a manufacturing process may be obtained.

Furthermore, when a separate auxiliary pulley is disposed as illustrated in FIG. 8, a separate structure, that is, a J16 pulley (not shown) and a J26 pulley 123J26, is additionally disposed to change the arrangement path of the first jaw wire 130J1 and the second jaw wire 130J2. Accordingly, the number of components is increased and the manufacturing process becomes complicated, and also the length of an end tool is increased as much as the size of the auxiliary pulley. However, in an embodiment of the disclosure, as the guide portion 125c is formed in the end tool hub 125, an effect of increasing the maximum rotation angle of an end tool without a separate additional structure may be obtained. Furthermore, as there is no need to additionally dispose a separate structure, the number of components is decreased and the manufacturing process is simplified, and also the length of an end tool is decreased as much as the size of an auxiliary pulley end tool so that the length of an end tool is decreased during a pitch motion. Accordingly, an effect of facilitating a surgical motion in a narrow space may be obtained.

The above effects are described below in detail.

Referring to FIG. 7, which illustrates a case in which no auxiliary pulley exists, as a first jaw wire 130J1' is fixedly coupled to a J11 pulley (not shown) and a second jaw wire 130J2' is fixedly coupled to a J21 pulley 123J21', when no auxiliary pulley is disposed, each of the J11 pulley and the J21 pulley 123J21' may be rotated by a line M of FIG. 7 in the arrow L direction. In other words, the J11 pulley (not shown) and the J21 pulley 123J21' are rotatable by only about a right angle where a fixing coupling portion 124' of the second jaw wire 130J2' and a J21 pulley 123J21' and the second jaw wire 130J2' are not separated. In this case, when an actuation motion is performed while the first jaw 121' and the second jaw 122' are located on the line M of FIG. 7, the first jaw 121' may be opened in the R direction, but the second jaw 122' may not be rotated beyond the line M in the L direction. Accordingly, when the first jaw 121' and the second jaw 122' perform a yaw motion over a certain angle, it is a problem that an actuation motion is not smoothly performed.

To address the above problem, in the surgical instrument 200 according to the related art in FIG. 8, a J16 pulley (not shown) and a J26 pulley 123J26", which are auxiliary pulleys, are additionally disposed at one side of the J11 pulley and a J21 pulley 123J21", respectively. As such, as the arrangement path of a first jaw wire 130J1" and a second jaw wire 130J2" is changed to a certain degree by disposing the J16 pulley and the J26 pulley 123J26", a tangential direction of the first jaw wire 130J1" and the second jaw wire 130J2" is changed. Accordingly, a fixing coupling portion 124" of the second jaw wire 130J2" and the J21 pulley 123J21" may be rotated by a line N of FIG. 8. However, in this case, in order to change the arrangement path of the first jaw wire 130J1" and the second jaw wire 130J2", a separate structure of the J16 pulley and the J26 pulley 123J26" are additionally disposed, and thus the number of components is increased and the manufacturing process becomes complicated, and also the length of an end tool is increased as much as the size of an auxiliary pulley. Accordingly, it is difficult to perform a motion in a narrow space.

To address the above problems, in the surgical instrument 100 according to an embodiment of the disclosure, as the guide portion 125c for changing the path of a wire is formed on an inner wall of the end tool hub 125, a feature of changing the arrangement path of a wire without a separate structure may be obtained. As such, as the arrangement path of the first jaw wire 130J1 and the second jaw wire 130J2 is changed to a certain degree by forming the guide portion 125c in the end tool hub 125, the tangential direction of the first jaw wire 130J1 and the second jaw wire 130J2 is changed. Accordingly, a fixing coupling portion 124 of the second jaw wire 130J2 and the J21 pulley 123J21 may be rotated by a line N of FIG. 9. In other words, the fixing coupling portion 124 of the second jaw wire 130J2 and the J21 pulley 123J21 is rotatable until the fixing coupling portion 124 is located on a common inner tangent line of the J21 pulley 123J21 and the J26 pulley 123J26. Likewise, a coupling portion of the first jaw wire 130J1 and the J11 pulley 123J11 is rotatable until the coupling portion is located on the common inner tangent line of the J11 pulley 123J11 and the J16 pulley 123J16, and thus the range of rotation may be increased in the R direction.

In other words, two stands of the first jaw wire 130J1 wound around the J11 pulley 123J11 by the guide portion 125c are disposed at one side with respect to the plane perpendicular to the Y-axis and passes through the X-axis. Simultaneously, two strands of the second jaw wire 130J2 wound around the J21 pulley 123J21 by the guide portion 125c are disposed at the other side with respect to the plane perpendicular to the Y-axis and passing through the X-axis In other words, the J12 pulley 123J12 and the J14 pulley 123J14 are disposed at one side with respect to the plane perpendicular to the Y-axis and passing through the X-axis, and the J22 pulley 123J22 and the J24 pulley 123J24 are disposed at the other side with respect to the plane perpendicular to the Y-axis and passing through the X-axis.

In other words, the first jaw wire 130J1 is located on the inner tangent line of the J11 pulley 123J11 and the guide portion 125c, and the rotation angle of the J11 pulley 123J11 is increased by the guide portion 125c. Furthermore, the second jaw wire 130J2 is located on the inner tangent line of the J21 pulley 123J21 and the guide portion 125c, and the rotation angle of the J21 pulley 123J21 is increased by the guide portion 125c.

In FIG. 10, (a) showing the end tool of the surgical instrument of FIG. 8 according to the related art and (b) showing the end tool of the surgical instrument of FIG. 4 according to an embodiment of the disclosure are compared with each other.

In comparison of (a) and (b) of FIG. 10, compared with the surgical instrument according to the related art of (a) of FIG. 10 where a separate auxiliary pulley 123J26' is formed, the end tool of the surgical instrument of the present disclosure of (b) of FIG. 10 where the guide portion 125c for changing the path of a wire is formed on the inner wall of the end tool hub 125, without forming an auxiliary pulley, has a length that is short by d. As such, as the length of an end tool is decreased, particularly when a pitch motion is performed, the length of an end tool is quite distinguished from the related art. Accordingly, when surgery is performed in a narrow surgery space in the human body, a surgical operator may easily manipulate a surgical instrument and a side effect of surgery may be reduced.

According to the present disclosure as above, as the rotation radii of the first jaw 121 and the second jaw 122 increase, a yaw motion range in which a normal opening/closing actuation motion is performed may be increased.

FIG. 11 illustrates a modified example of the end tool of FIG. 4.

A surgical instrument according to the present modified example is characteristically different from the above-described surgical instrument according to the embodiment of the present disclosure in that the separate guide groove (see 125d of FIG. 6) is not formed in the guide portion 125c of the end tool hub 125. As such, as the separate guide groove (see 125d of FIG. 6) is not formed, the manufacturing process may be further simplified and manufacturing costs may be reduced.

(Manipulation Portion)

Figure 12:
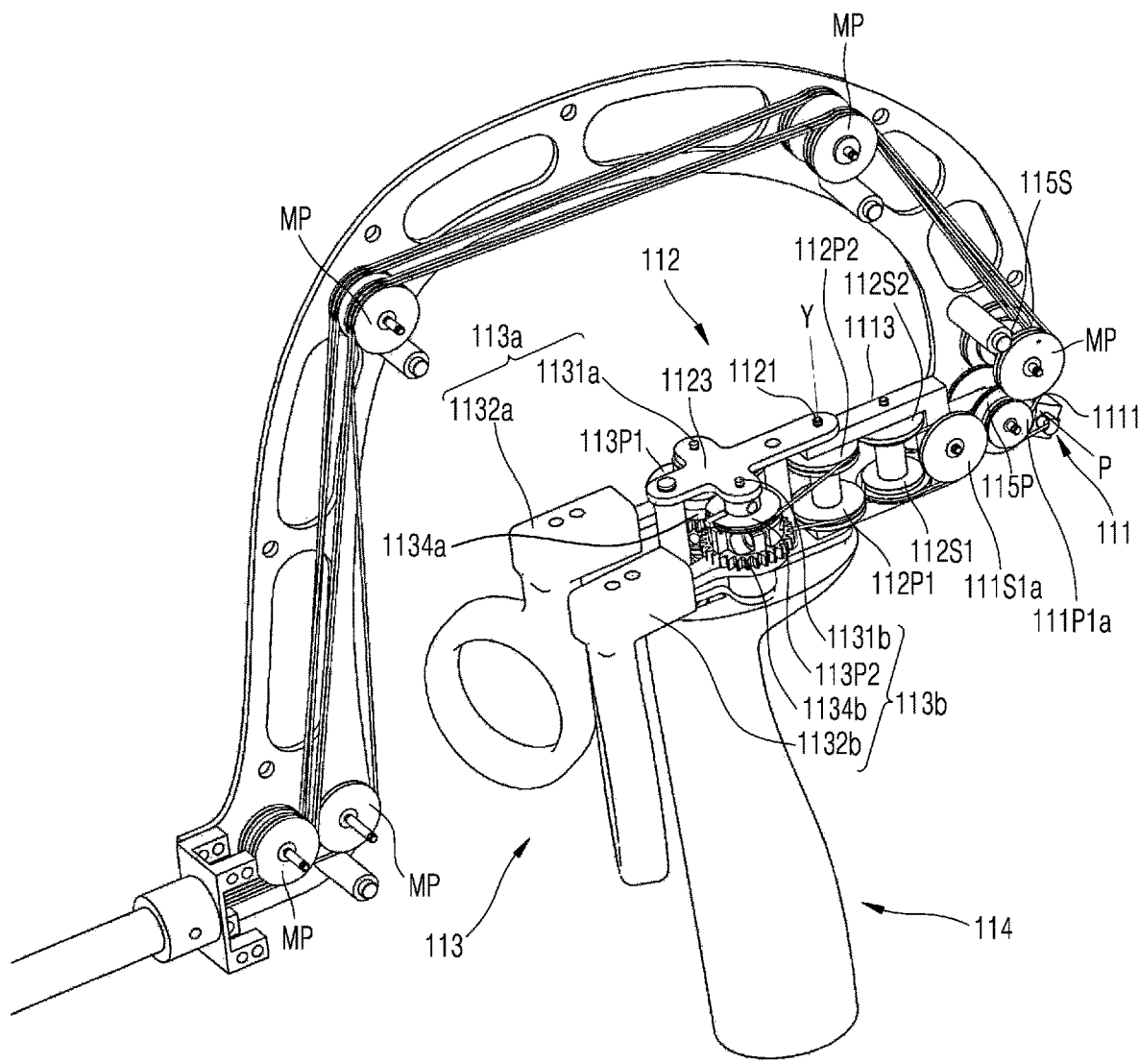
FIGS. 12 and 13 are perspective views of the manipulation portion of the surgical instrument of FIG. 2.
Figure 13:
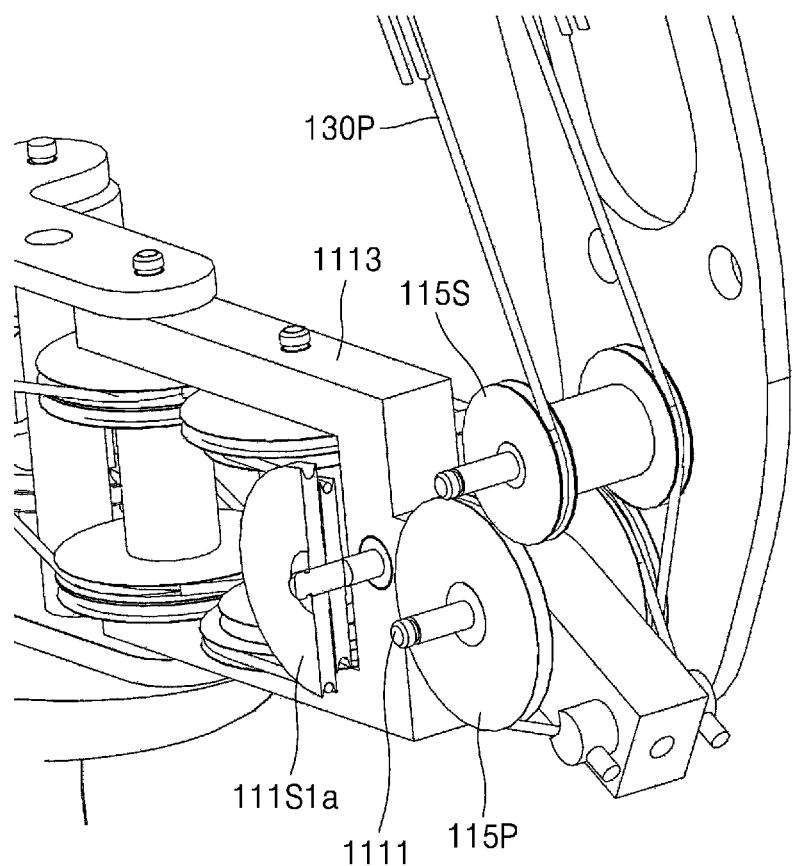

FIG. 12 is a perspective view of the manipulation portion of the surgical instrument of FIG. 2, and FIG. 13 is a perspective view of FIG. 12 viewed from the rear side.

Referring to FIGS. 2 to 13, the manipulation portion 110 of the surgical instrument 100 according to an embodiment of the disclosure may include the first handle 114 that a user may grip, the actuation manipulation portion 113 for controlling the actuation motion of the end tool 120, the yaw manipulation portion 112 for controlling the yaw motion of the end tool 120, and the pitch manipulation portion 111 for controlling the pitch motion of the end tool 120.

First, in an example of a use stage of the surgical instrument 100 of FIG. 2, while a user grips the first handle 114 in the palm, the first handle 114 is rotated around the Y-axis, that is, the pitch rotation shaft 1111, to perform a pitch motion, and the first handle 114 is rotated around the Z-axis, that is, a yaw rotation shaft 1121, to perform a yaw motion. Furthermore, the user may perform an actuation motion by rotating the actuation manipulation portion 113 with a thumb and an index finger inserted into the actuation manipulation portion 113.

In the surgical instrument 100 according to an embodiment of the disclosure, when the manipulation portion 110 is rotated in one direction with respect to the connection portion 140, the end tool 120 is characteristically rotated in the intuitively same direction as the manipulating direction of the manipulation portion 110. In other words, when the first handle 114 of the manipulation portion 110 is rotated in any one direction, the end tool 120 is also rotated in the intuitively same direction as the one direction, thereby performing a pitch motion or a yaw motion. The intuitively same direction may means that a direction in which the finger of a user gripping the manipulation portion 110 moves and a direction in which an end portion of the end tool 120 moves form substantially the same direction. The same direction may not be a perfectly matching direction in 3 dimension coordinates, and may be understood to be sameness to a degree that, for example, when a user's finger moves to the left, the end portion of the end tool 120 also moves to the left, and when the user's finger moves downwards, the end portion of the end tool 120 also moves downwards.

To this end, in the surgical instrument 100 according to an embodiment of the disclosure, the manipulation portion 110 and the end tool 120 is characteristically formed in the same direction with respect to a plane perpendicular to an extension-axis of the connection portion 140. In other words, when viewed based on the Y-Z plane of FIG. 2, the manipulation portion 110 extends in a +X-axis direction, and simultaneously the end tool 120 also extends in the +X-axis direction. In other words, a direction in which the end tool 120 is formed in the one end portion of the connection portion 140 and a direction in which the manipulation portion 110 is formed the other end portion of the connection portion 140 may be the same direction with respect to the Y-Z plane. Alternatively, in other words, it may be said that the manipulation portion 110 is formed in a direction away from a body of a user who grips the manipulation portion 110, that is, toward a direction in which the end tool 120 is formed. In other words, the first handle 114, actuation rotating portions 1132a and 1132b, and the like, which are moved by being gripped by a user for an actuation motion, a yaw motion, and a pitch motion, are formed such that a portion moving for performing each motion is formed to extend in the +X-axis direction than a rotation center of each joint for the motion. Accordingly, as the manipulation portion 110 may be configured in the same manner in which a moving portion of the end tool 120 is formed to extend in the +X-axis direction than the rotation center of each joint for the motion, as described in FIG. 1, the user's manipulating direction and the end tool's motion direction are matched with each other both in view of the rotating direction and in view of the left and right directions. Consequently, the intuitively same manipulation may be possible.

In detail, for the surgical instrument according to the related art, as a direction in which a user manipulates a manipulation portion and the end tool's actual manipulation direction are different from each other and are not intuitively matched with each other, the intuitive operation is not easy in view of a surgical operator, and it takes long to be skilled to move the end tool in a desired direction. In some cases, malfunction may be generated so that a patient is damaged.

To address the above problem, in the surgical instrument 100 according to an embodiment of the disclosure, the manipulating direction of the manipulation portion 110 and the manipulation direction of the end tool 120 are intuitively the same direction. To this end, the manipulation portion 110, like the end tool 120, is characteristic in that an actually moving portion for an actuation motion, a yaw motion, and a pitch motion is formed to extend in the +X-axis direction than the rotation center of the joint of each motion, which is described below in detail.

The first handle 114 may be formed to be gripped by a user with a hand, particularly by wrapping the first handle 114 with his/her palm. The actuation manipulation portion 113 and the yaw manipulation portion 112 may be formed on the first handle 114, and the pitch manipulation portion 111 may be formed at one side of the yaw manipulation portion 112. The other end portion of the pitch manipulation portion 111 may be connected to the bent portion 141 of the connection portion 140.

The actuation manipulation portion 113 may include a first actuation manipulation portion 113*a* and a second actuation manipulation portion 113*b*. The first actuation manipulation portion 113*a* may include a first actuation rotation shaft 1131*a*, a first actuation rotating portion 1132*a*, a first actuation pulley 113P1, and a first actuation gear 1134*a*. The second actuation manipulation portion 113*b* may include a second actuation rotation shaft 1131*b*, a second actuation rotating portion 1132*b*, a second actuation pulley 113P2, and a second actuation gear 1134*b*. The first actuation rotating portion 1132*a* and the second actuation rotating portion 1132*b* may be operated by means of a second handle.

The actuation rotation shafts 1131*a* and 1131*b* may be formed at a certain angle with respect to the X-Y plane where the connection portion 140 is formed. For example, the actuation rotation shafts 1131*a* and 1131*b* may be formed in a direction parallel to the Z-axis, and in this state, when the pitch manipulation portion 111 or the yaw manipulation portion 112 is rotated, the coordinate system of the actuation manipulation portion 113 may be changed relative thereto. The concept of the present disclosure is not limited thereto, and the actuation rotation shafts 1131*a* and 1131*b* may be formed in various directions suitable for the structure of a hand of a user gripping the actuation manipulation portion 113 according to an ergonomic design.

The first actuation rotating portion 1132*a*, the first actuation pulley 113P1, and the first actuation gear 1134*a* are fixed coupled to one another to be rotatable together around the first actuation rotation shaft 1131*a*. The first actuation pulley 113P1 may be configured to be a single pulley or two pulleys fixedly coupled to each other.

Likewise, the second actuation rotating portion 1132*b*, the second actuation pulley 113P2, and the second actuation gear 1134*b* are fixedly coupled to one another to be rotatable together around the second actuation rotation shaft 1131*b*. The second actuation pulley 113P2 may be configured to be a single pulley or two pulleys fixedly coupled to each other.

The first actuation gear 1134*a* and the second actuation gear 1134*b* may be formed to be engaged with each other such that, when any one gear rotates, the other rotates in the opposite direction.

The yaw manipulation portion 112 may include the yaw rotation shaft 1121, a first jaw yaw pulley 112P1, a second jaw yaw pulley 112P2, and a yaw frame 1123. Furthermore, the yaw manipulation portion 112 may further include a first jaw yaw auxiliary pulley 112S1 formed at one side of the first jaw yaw pulley 112P1, and a second jaw yaw auxiliary pulley 112S2 formed at one side of the second jaw yaw pulley 112P2. The first jaw yaw auxiliary pulley 112S1 and the second jaw yaw auxiliary pulley 112S2 may be coupled to a pitch frame 1113 that is described below.

Although the drawings illustrate that the yaw manipulation portion 112 includes the first jaw yaw pulley 112P1 and the second jaw yaw pulley 112P2, and that the first jaw yaw pulley 112P1 and the second jaw yaw pulley 112P2 each includes two pulleys formed to face each other and capable of independently rotating, the concept of the present disclosure is not limited thereto. In other words, one or more pulleys having the same or different diameters may be provided according to the configuration of the yaw manipulation portion 112.

In detail, the yaw rotation shaft 1121 is formed at one side of the actuation manipulation portion 113 on the first handle 114. In this state, the first handle 114 may be formed to be capable of rotating around the yaw rotation shaft 1121.

The yaw rotation shaft 1121 may be formed at an angle with respect to the X-Y plane where the connection portion 140 is formed. For example, the yaw rotation shaft 1121 may be formed in a direction parallel to the Z-axis, and in this state, when the pitch manipulation portion 111 rotates, the coordinate system of the yaw rotation shaft 1121 may be changed relative thereto as described above. The concept of the present disclosure is not limited thereto, and the yaw rotation shaft 1121 may be formed in various directions suitable for the structure of a hand of a user gripping the manipulation portion 110 according to an ergonomic design.

The first jaw yaw pulley 112P1 and the second jaw yaw pulley 112P2 are coupled to the yaw rotation shaft 1121 to be capable of rotating around the yaw rotation shaft 1121. The first jaw wire 130J1 may be wound around the first jaw yaw pulley 112P1, and the second jaw wire 130J2 may be wound around the second jaw yaw pulley 112P2. In this state, the first jaw yaw pulley 112P1 and the second jaw yaw pulley 112P2 each may be formed, as two pulleys, to face each other and to be capable of independently rotating. Accordingly, a wire being wound and a wire being released may be wound around separate pulleys so that the wires perform motions without interference with each other.

The yaw frame 1123 may connect the first handle 114, the yaw rotation shaft 1121, the first actuation rotation shaft 1131*a*, and the second actuation rotation shaft 1131*b*, to allow the first handle 114, the yaw manipulation portion 112, and the actuation manipulation portion 113 to be integrally rotated around the yaw rotation shaft 1121.

The pitch manipulation portion 111 may include the pitch rotation shaft 1111, a first jaw pitch pulley-a 111P1*a*, a first jaw pitch pulley-b 111P1*b* (not shown), a second jaw pitch pulley-a 111P2*a* (not shown), a second jaw pitch pulley-b 111P2*b* (not shown), and a pitch frame 1113. Furthermore, the pitch manipulation portion 111 may further include a first jaw pitch auxiliary pulley-a 111S1*a* formed at one side of the first jaw pitch pulley-a 111P1*a*, a first jaw pitch auxiliary pulley-b 111S1*b* (not shown) formed at one side of the first jaw pitch pulley-b 111P1*b*, a second jaw pitch auxiliary pulley-a 111S2*a* (not shown) formed at one side of the second jaw pitch pulley-a 111P2*a*, and a second jaw pitch auxiliary pulley-b 111S2*b* (not shown) formed at one side of the second jaw pitch pulley-b 111P2*b*. The pitch manipulation portion 111 is connected to the bent portion 141 of the connection portion 140 via the pitch rotation shaft 1111.

In detail, the pitch frame 1113 is a base frame of the pitch manipulation portion 111, and the yaw rotation shaft 1121 is rotatably coupled to one end portion thereof. In other words, the yaw frame 1123 is rotatable around the yaw rotation shaft 1121 with respect to the pitch frame 1113.

As described above, the yaw frame 1123 connects the first handle 114, the yaw rotation shaft 1121, the first actuation rotation shaft 1131a, and the second actuation rotation shaft 1131b, and also, as the yaw frame 1123 is connected to the pitch frame 1113, when the pitch frame 1113 rotates around the pitch rotation shaft 1111, the yaw frame 1123 connected to the pitch frame 1113, the first handle 114, the yaw rotation shaft 1121, the first actuation rotation shaft 1131a, and the second actuation rotation shaft 1131b are rotated together. In other words, when the pitch manipulation portion 111 is rotated around the pitch rotation shaft 1111, the actuation manipulation portion 113 and the yaw manipulation portion 112 are rotated together with the pitch manipulation portion 111. In other words, when a user pitch-rotates the first handle 114 around the pitch rotation shaft 1111, the actuation manipulation portion 113, the yaw manipulation portion 112, and the pitch manipulation portion 111 are moved together.

The pitch rotation shaft 1111, the first jaw pitch pulley-a 111P1a, the first jaw pitch pulley-b 111P1b, the second jaw pitch pulley-a 111P2a, and the second jaw pitch pulley-b 111P2b are coupled to the pitch frame 1113. In this state, the first jaw pitch pulley-a 111P1a, the first jaw pitch pulley-b 111P1b, the second jaw pitch pulley-a 111P2a, and the second jaw pitch pulley-b 111P2b are coupled to the pitch rotation shaft 1111 to be capable of rotating around the pitch rotation shaft 1111.

The first jaw pitch pulley-a 111P1a and the first jaw pitch pulley-b 111P1b may be formed to face each other and to be capable of independently rotating. Accordingly, a wire being wound and a wire being released may be wound around separate pulleys so that the wires perform motions without interference with each other. Likewise, the second jaw pitch pulley-a 111P2a and the second jaw pitch pulley-b 111P2b may also be formed to face each other and to be capable of independently rotating. Accordingly, a wire being wound and a wire being released may be wound around separate pulleys so that the wires perform motions without interference with each other.

Referring to FIG. 13, the pitch wire end pulley 115P is fixedly coupled to the pitch frame 1113 to be rotatable together. The pitch wire 130P is fixedly coupled to the pitch frame 1113 via a pitch wire auxiliary pulley 115S and the pitch wire end pulley 115P. Consequently, the pitch frame 1113 and the pitch wire end pulley 115P may be rotated together around the pitch rotation shaft 1111 according to the pitch rotation.

A motion of the pitch wire 130P is described below.

The pitch pulley 123P is fixedly coupled to the end tool hub 125 in the end tool 120, the pitch wire end pulley 115P is formed in the manipulation portion 110, and the pitch pulley 123P and the pitch wire end pulley 115P are connected to each other by the pitch wire 130P, so that the pitch motion of the end tool 120 is easily performed according to the pitch manipulation of the manipulation portion 110. Both end portions of the pitch wire 130P are fixedly coupled to the pitch frame 1113 respectively via the pitch wire auxiliary pulley 115S and the pitch wire end pulley 115P, and the pitch wire end pulley 115P is fixedly coupled to the pitch frame 1113. In other words, the pitch frame 1113 and the pitch wire end pulley 115P are rotated together around the pitch rotation shaft 1111 by the pitch rotation of the manipulation portion 110. Consequently, both end portions of the pitch wire 130P are moved in the opposite directions, and thus a driving force of additional pitch rotation separate from the pitch motion of the end tool 120 by the first jaw wire 130J1 and the second jaw wire 130J2 may be transmitted.

A relationship between the first handle 114 and each of the pitch manipulation portion 111, the yaw manipulation portion 112, and the actuation manipulation portion 113 is summarized as follows. The actuation rotation shafts 1131a and 1131b, the yaw rotation shaft 1121, and the pitch rotation shaft 1111 may be formed on the first handle 114. In this state, as the actuation rotation shafts 1131a and 1131b are directly formed on the first handle 114, the first handle 114 and the actuation manipulation portion 113 may be directly connected to each other. As the yaw rotation shaft 1121 is directly formed on the first handle 114, the first handle 114 and the yaw manipulation portion 112 may be directly connected to each other. In contrast, as the pitch manipulation portion 111 is formed at one side of the yaw manipulation portion 112 to be connected to the yaw manipulation portion 112, the pitch manipulation portion 111 is not directly connected to the first handle 114, and the pitch manipulation portion 111 and the first handle 114 may be indirectly connected to each other via the yaw manipulation portion 112.

Referring back to the drawing, in the surgical instrument 100 according to an embodiment of the disclosure, the pitch manipulation portion 111 and the end tool 120 may be formed on the same or parallel axis (X-axis). In other words, the pitch rotation shaft 1111 of the pitch manipulation portion 111 is formed on one end portion of the bent portion 141 of the connection portion 140, and the end tool 120 is formed on the other end portion of the connection portion 140.

One or more intermediate pulleys MP for changing or guiding paths of wires may be disposed at some places along the connection portion 140, particularly in the bent portion 141. As the wires are at least partially wound around the intermediate pulleys MP to guide the paths of the wires, the wires may be disposed along a bent shape of the bent portion 141.

Although the connection portion 140 is illustrated to have the bent portion 141 to be curved with a certain radius of curvature, the concept of the present disclosure is not limited thereto, and the connection portion 140 may be formed linearly or to be bent one or more times, as necessary. Even in this case, it may be said that the pitch manipulation portion 111 and the end tool 120 are formed on substantially the same or parallel axis. Furthermore, although FIG. 3 illustrates that the pitch manipulation portion 111 and the end tool 120 each are formed on an axis parallel to the X-axis, the concept of the present disclosure is not limited thereto, and the pitch manipulation portion 111 and the end tool 120 may be formed on different axes.

The actuation motion, the yaw motion, and the pitch motion according to the present embodiment are described below.

First, the actuation motion is described as follows.

When a user inserts an index finger into the first actuation rotating portion 1132a and a thumb into the second actuation rotating portion 1132b and rotates the first and second actuation rotating portions 1132a and 1132b by using any one finger or both fingers, the first actuation pulley 113P1 fixedly coupled to the first actuation rotating portion 1132a and the first actuation gear 1134a are rotated around the first actuation rotation shaft 1131a, and the second actuation pulley 113P2 fixedly coupled to the second actuation rotating portion 1132b and the second actuation gear 1134b are rotated around the second actuation rotation shaft 1131b. In this state, the first actuation pulley 113P1 and the second actuation pulley 113P2 are rotated in the opposite directions. Accordingly, the first jaw wire 130J1 wound around the first actuation pulley 113P1 with one end portion thereof fixedly coupled thereto and the second jaw wire 130J2 wound around the second actuation pulley 113P2 with one end portion thereof fixedly coupled thereto are also moved in the opposite directions. As the above rotation force is transmitted to the end tool 120 via the driving force transmission portion 130, the two jaws 121 and 122 of the end tool 120 perform an actuation motion. The actuation motion may mean a motion of the two jaws 121 and 122 rotating in the opposite directions being opened or closed, as described above. In other words, when the first and second actuation rotating portions 1132a and 1132b of the actuation manipulation portion 113 are rotated in directions close to each other, the first jaw 121 is rotated counterclockwise and the second jaw 122 is rotated clockwise so that the end tool 120 is closed, and when the first and second actuation rotating portions 1132a and 1132b of the actuation manipulation portion 113 are rotated in directions away from each other, the first jaw 121 is rotated clockwise and the second jaw 122 is rotated counterclockwise so that the end tool 120 is opened. In the present embodiment, as the first actuation rotating portion 1132a and the second actuation rotating portion 1132b, forming the second handle, are provided for the above-described actuation manipulation, the actuation manipulation may be performed by using two fingers. However, the configuration of the actuation manipulation portion 113 for the actuation manipulation of opening or closing the two jaws of the end tool 120 may be sufficiently modified such that, for example, two actuation pulleys (the first actuation pulley 113P1 and the second actuation pulley 113P2) may be reversely rotated by using one actuation rotation portion, unlike the above description.

Next, the yaw motion is described as follows.

When a user grips the first handle 114 and rotates the first handle 114 around the yaw rotation shaft 1121, the actuation manipulation portion 113 and the yaw manipulation portion 112 perform a yaw rotation around the yaw rotation shaft 1121. In other words, when the first actuation pulley 113P1 of the first actuation manipulation portion 113a to which the first jaw wire 130J1 is fixedly coupled is rotated around the yaw rotation shaft 1121, the first jaw wire 130J1 wound around the first jaw yaw pulley 112P1 is moved. Likewise, when the second actuation pulley 113P2 of the second actuation manipulation portion 113b to which the second jaw wire 130J2 is fixedly coupled is rotated around the yaw rotation shaft 1121, the second jaw wire 130J2 wound around the second jaw yaw pulley 112P2 is moved. In this state, the first jaw wire 130J1 connected to the first jaw 121 and the second jaw wire 130J2 connected to the second jaw 122 are respectively wound around the first jaw yaw pulley 112P1 and the second jaw yaw pulley 112P2 so that, during a yaw rotation, the first jaw 121 and the second jaw 122 are rotated in the same direction. As the rotation force is transmitted to the end tool 120 via the driving force transmission portion 130, the two jaws 121 and 122 of the end tool 120 perform a yaw motion rotating in the same direction.

In this state, as the yaw frame 1123 connects the first handle 114, the yaw rotation shaft 1121, the first actuation rotation shaft 1131a, and the second actuation rotation shaft 1131b to one another, the first handle 114, the yaw manipulation portion 112, and the actuation manipulation portion 113 are rotated around the yaw rotation shaft 1121 together.

Next, the pitch motion is described as follows.

When a user grips the first handle 114 and rotates the first handle 114 around the pitch rotation shaft 1111, the actuation manipulation portion 113, the yaw manipulation portion 112, and the pitch manipulation portion 111 perform a pitch rotation around the pitch rotation shaft 1111. In other words, the first actuation pulley 113P1 of the first actuation manipulation portion 113a to which the first jaw wire 130J1 is fixedly coupled is rotated around the pitch rotation shaft 1111, the first jaw wire 130J1 wound around the first jaw pitch pulley-a 111P1a and the first jaw pitch pulley-b 111P1b is moved. Likewise, when the second actuation pulley 113P2 of the second actuation manipulation portion 113b to which the second jaw wire 130J2 is fixedly coupled is rotated around the pitch rotation shaft 1111, the second jaw wire 130J2 wound around the second jaw pitch pulley-a 111P2a and the second jaw pitch pulley-b 111P2b is moved. In this state, as described above in FIG. 9, as both strands of the first jaw wire 130J1 are moved in the same direction and both strands of the second jaw wire 130J2 are moved in the same direction, the first jaw wire 130J1 and the second jaw wire 130J2 are wound around the first jaw pitch pulleys 111P1a and 111P1b and the second jaw pitch pulleys 111P2a and 111P2b so that the first jaw 121 and the second jaw 122 may perform a pitch rotation. As the rotation force is transmitted to the end tool 120 via the driving force transmission portion 130, the two jaws 121 and 122 of the end tool 120 perform a pitch motion.

In this state, as the pitch frame 1113 is connected to the yaw frame 1123 and the yaw frame 1123 connects the first handle 114, the yaw rotation shaft 1121, the first actuation rotation shaft 1131a, and the second actuation rotation shaft 1131b to one another, when the pitch frame 1113 is rotated around the pitch rotation shaft 1111, the yaw frame 1123 connected to the pitch frame 1113, the first handle 114, the yaw rotation shaft 1121, the first actuation rotation shaft 1131a, and the second actuation rotation shaft 1131b are rotated together. In other words, when the pitch manipulation portion 111 is rotated around the pitch rotation shaft 1111, the actuation manipulation portion 113 and the yaw manipulation portion 112 are rotated together with the pitch manipulation portion 111.

In summary, it is the characteristics of the surgical instrument 100 according to an embodiment of the disclosure that a pulley is provided at each joint point (actuation joint, yaw joint, or pitch joint), a wire (first jaw wire or second jaw wire) is wound around the pulley, a rotation manipulation (actuation rotation, yaw rotation, or pitch rotation) of a manipulation portion causes a movement of each wire, and thus a desired motion of the end tool 120 is induced. Furthermore, as auxiliary pulleys may be provided at one side of each pulley, the auxiliary pulleys may prevent the wire from being wound around one pulley multiple times.

Figure 14:
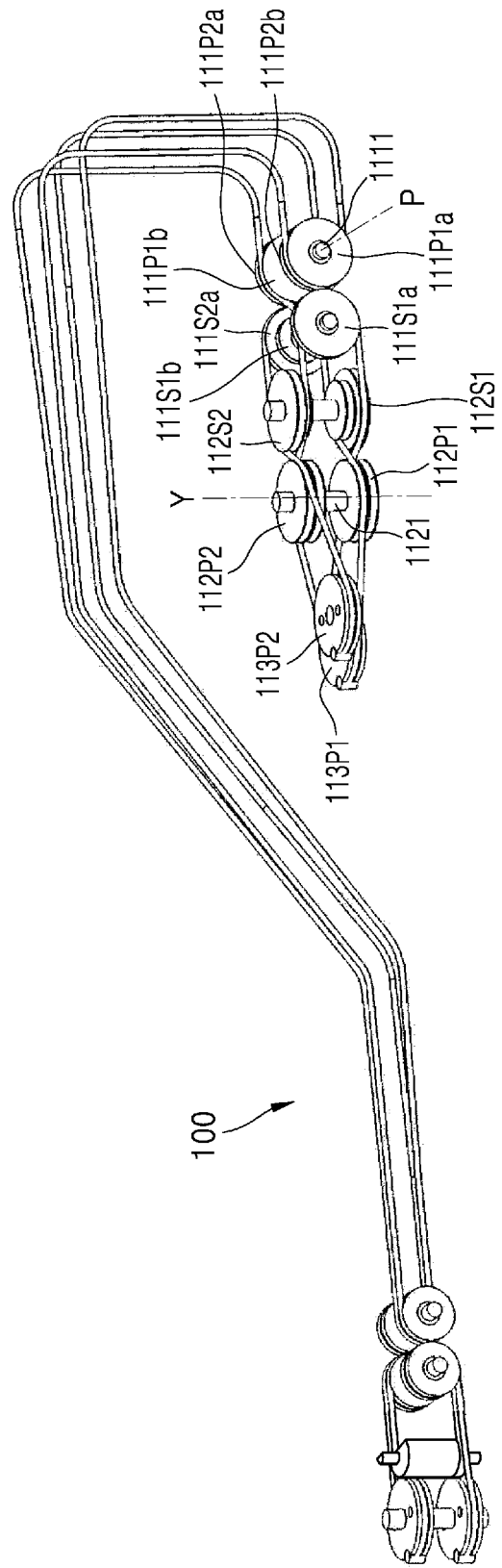
FIG. 14 schematically illustrates only a configuration of pulleys and wires forming a joint of the surgical instrument of FIG. 12 according to an embodiment of the disclosure.

FIG. 14 schematically illustrates only a configuration of pulleys and wires forming a joint of the surgical instrument 100 of FIG. 12 according to an embodiment of the disclosure. In FIG. 14, the intermediate pulleys for changing the paths of the wires are omitted regardless of the joint motion.

Referring to FIG. 14, the manipulation portion 110 may include the first actuation pulley 113P1, the first jaw yaw pulley 112P1, the first jaw yaw auxiliary pulley 112S1, the first jaw pitch pulley-a 111P1a, the first jaw pitch pulley-b 111P1b, the first jaw pitch auxiliary pulley-a 111S1a, and the first jaw pitch auxiliary pulley-b 111S1b, which are related to the rotating motion of the first jaw 121.

Furthermore, the manipulation portion 110 may include the second actuation pulley 113P2, the second jaw yaw pulley 112P2, the second jaw yaw auxiliary pulley 112S2, the second jaw pitch pulley-a 111P2a, the second jaw pitch pulley-b 111P2b, the second jaw pitch auxiliary pulley-a 111S2a, and the second jaw pitch auxiliary pulley-b 111S2b, which are related to the rotating motion of the second jaw 122. (As the arrangement and configuration of the respective pulleys in the manipulation portion 110 are the same in principle as those of the respective pulleys in the end tool 120, detailed indications of reference numerals on the drawing are partially omitted.)

The first jaw yaw pulley 112P1 and the second jaw yaw pulley 112P2 may be formed to be capable of independently rotating around the yaw rotation shaft 1121 that is the same axis. In this state, the first jaw yaw pulley 112P1 and the second jaw yaw pulley 112P2 may be formed, as two pulleys, to face each other and to be capable of independently rotating.

The first jaw yaw auxiliary pulley 112S1 and the second jaw yaw auxiliary pulley 112S2 may be formed to be capable of independently rotating around the same axis. In this state, the first jaw yaw auxiliary pulley 112S1 may be formed, as two pulleys, to face each other and to be capable of independently rotating, and in this state, the two pulleys may have different diameters. Likewise, the second jaw yaw auxiliary pulley 112S2 may be formed, as two pulleys, to face each other and to be capable of independently rotating, and in this state, the two pulleys may have different diameters.

The first jaw pitch auxiliary pulley-a 111S1a, the first jaw pitch auxiliary pulley-b 111S1b, the second jaw pitch auxiliary pulley-a 111S2a, and the second jaw pitch auxiliary pulley-b 111S2b may be formed to be capable of independently rotating around the same axis. In this state, the first jaw pitch auxiliary pulley-a 111S1a and the first jaw pitch auxiliary pulley-b 111S1b may have different diameters. Furthermore, the second jaw pitch auxiliary pulley-a 111S2a and the second jaw pitch auxiliary pulley-b 111S2b may have different diameters.

The first jaw pitch pulley-a 111P1a, the first jaw pitch pulley-b 111P1b, the second jaw pitch pulley-a 111P2a, and the second jaw pitch pulley-b 111P2b may be formed to be capable of independently rotating around the pitch rotation shaft 1111 that is the same axis.

The first jaw wire 130J1 is formed to sequentially pass the first jaw pitch pulley-a 111P1a, the first jaw pitch auxiliary pulley-a 111S1a, the first jaw yaw auxiliary pulley 112S1, and the first jaw yaw pulley 112P1 of the manipulation portion 110 to be wound around the first actuation pulley 113P1, and then sequentially pass again the first jaw yaw pulley 112P1, the first jaw yaw auxiliary pulley 112S1, the first jaw pitch auxiliary pulley-b 111S1b, and the first jaw pitch pulley-b 111P1b, and to move along the pulleys while the first jaw wire 130J1 rotates the pulleys. In this state, the first jaw wire 130J1 may be fixedly coupled to one point of the first actuation pulley 113P1.

The second jaw wire 130J2 is formed to sequentially pass the second jaw pitch pulley-a 111P2a, the second jaw pitch auxiliary pulley-a 111S2a, the second jaw yaw auxiliary pulley 112S2, and the second jaw yaw pulley 112P2 of the manipulation portion 110 to be wound around the second actuation pulley 113P2, and then sequentially pass again the second jaw yaw pulley 112P2, the second jaw yaw auxiliary pulley 112S2, the second jaw pitch auxiliary pulley-b 111S2b, and the second jaw pitch pulley-b 111P2b, and to move along the pulleys while the second jaw wire 130J2 rotates the pulleys. In this state, the second jaw wire 130J2 may be fixedly coupled to one point of the second actuation pulley 113P2.

Figure 16:
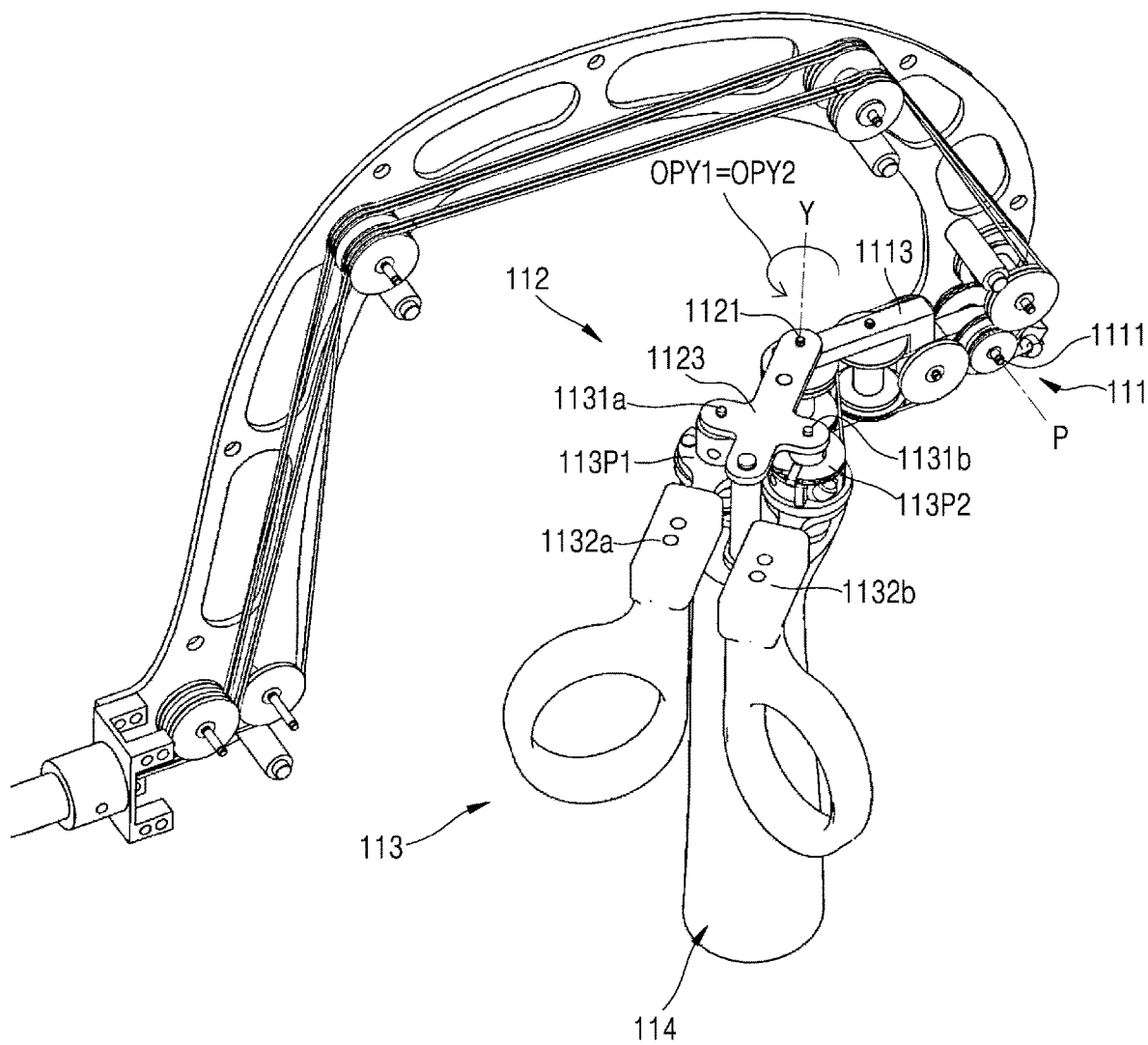
FIG. 16 is a perspective view of a yaw motion of the surgical instrument of FIG. 12.

FIGS. 15A-15B schematically illustrate a configuration of pulleys and wires related to an actuation motion and a yaw motion of the surgical instrument 100 of FIG. 12 according to an embodiment of the disclosure, for a first jaw and a second jaw. FIG. 15A illustrates pulleys and wires only for the second jaw, and FIG. 15B illustrates pulleys and wires only for the first jaw. FIG. 16 is a perspective view of a yaw motion of the surgical instrument of FIG. 12.

First, a wire motion of the actuation motion is described below.

Referring to FIG. 15B, when the first actuation rotating portion 1132a is rotated around the first actuation rotation shaft 1131a in an arrow OPA1 direction, the first actuation pulley 113P1 connected to the first actuation rotating portion 1132a is rotated, and thus both strands of the first jaw wire 130J1 wound around the first actuation pulley 113P1 are moved in directions W1a and W1b, Consequently, the first jaw 121 of the manipulation portion 110 is rotated in an arrow EPA1 direction.

Referring to FIG. 15A, when the second actuation rotating portion 1132b is rotated around the second actuation rotation shaft 1131b in an arrow OPA2 direction, the second actuation pulley 113P2 connected to the second actuation rotating portion 1132b is rotated, and thus both strands of the second jaw wire 130J2 wound around the second actuation pulley 113P2 are moved in directions W2a and W2b. Consequently, the second jaw 122 of the manipulation portion 110 is rotated in an arrow EPA2 direction. Accordingly, when a user manipulates the first actuation rotating portion 1132a and the second actuation rotating portion 1132b in directions close to each other, a motion of the first jaw 121 and the second jaw 122 of the end tool 120 being close to each other is performed.

Next, a wire motion of the yaw motion is described below.

First, as the yaw rotation shaft 1121, the first actuation rotation shaft 1131a, and the second actuation rotation shaft 1131b are connected to by the yaw frame (see 1123 of FIG. 12), the yaw rotation shaft 1121, the first actuation rotation shaft 1131a, and the second actuation rotation shaft 1131b are integrally rotated together.

Referring to FIG. 15B, when the first handle 114 is rotated around the yaw rotation shaft 1121 in an arrow OPY1 direction, the first actuation pulley 113P1 and the first jaw yaw pulley 112P1, and the first jaw wire 130J1 wound therearound, are rotated as a whole around the yaw rotation shaft 1121. Consequently, both strands of the first jaw wire 130J1 wound around the first jaw yaw pulley 112P1 are moved in the directions W1a and W1b, respectively. As a result, the first jaw 121 of the end tool 120 is rotated in an arrow EPY1 direction.

Referring to FIG. 15A, when the first handle 114 is rotated around the yaw rotation shaft 1121 in an arrow OPY2 direction, the second actuation pulley 113P2 and the second jaw yaw pulley 112P2, and the second jaw wire 130J2 wound therearound, are rotated as a whole around the yaw rotation shaft 1121, Consequently, both strands of the second jaw wire 130J2 wound around the second jaw yaw pulley 112P2 are respectively moved in a direction opposite to the direction W1a and a direction opposite to the direction W1b. As a result, the first jaw 121 of the end tool 120 is rotated in an arrow EPY2 direction.

Figure 17A:
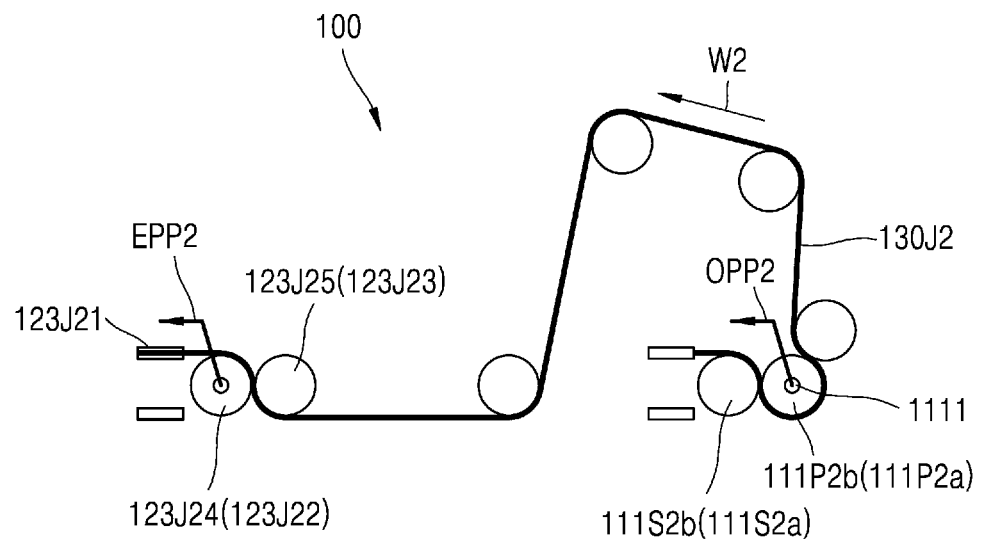
FIGS. 17A and 17B schematically illustrate a configuration of pulleys and wires related to a pitch motion of the surgical instrument of FIG. 12 according to an embodiment of the disclosure, for a first jaw and a second jaw.
Figure 17B:
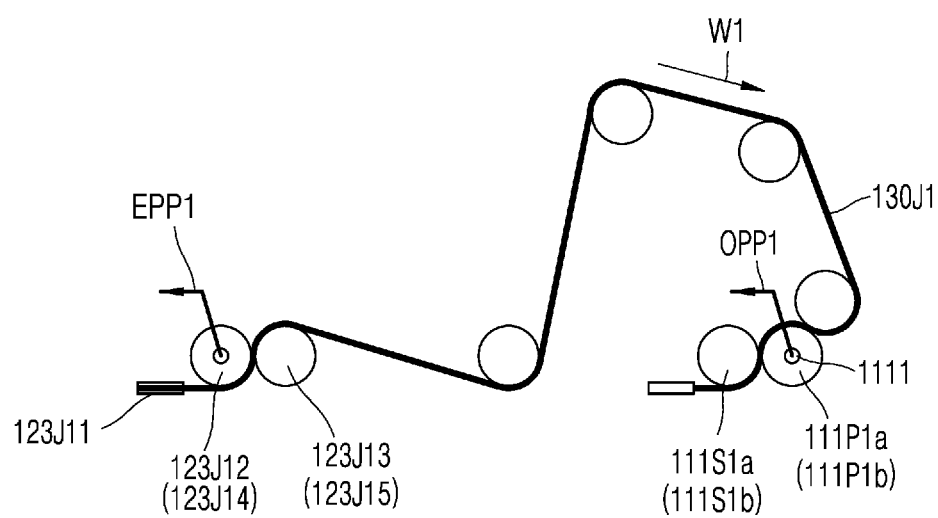
Figure 18:
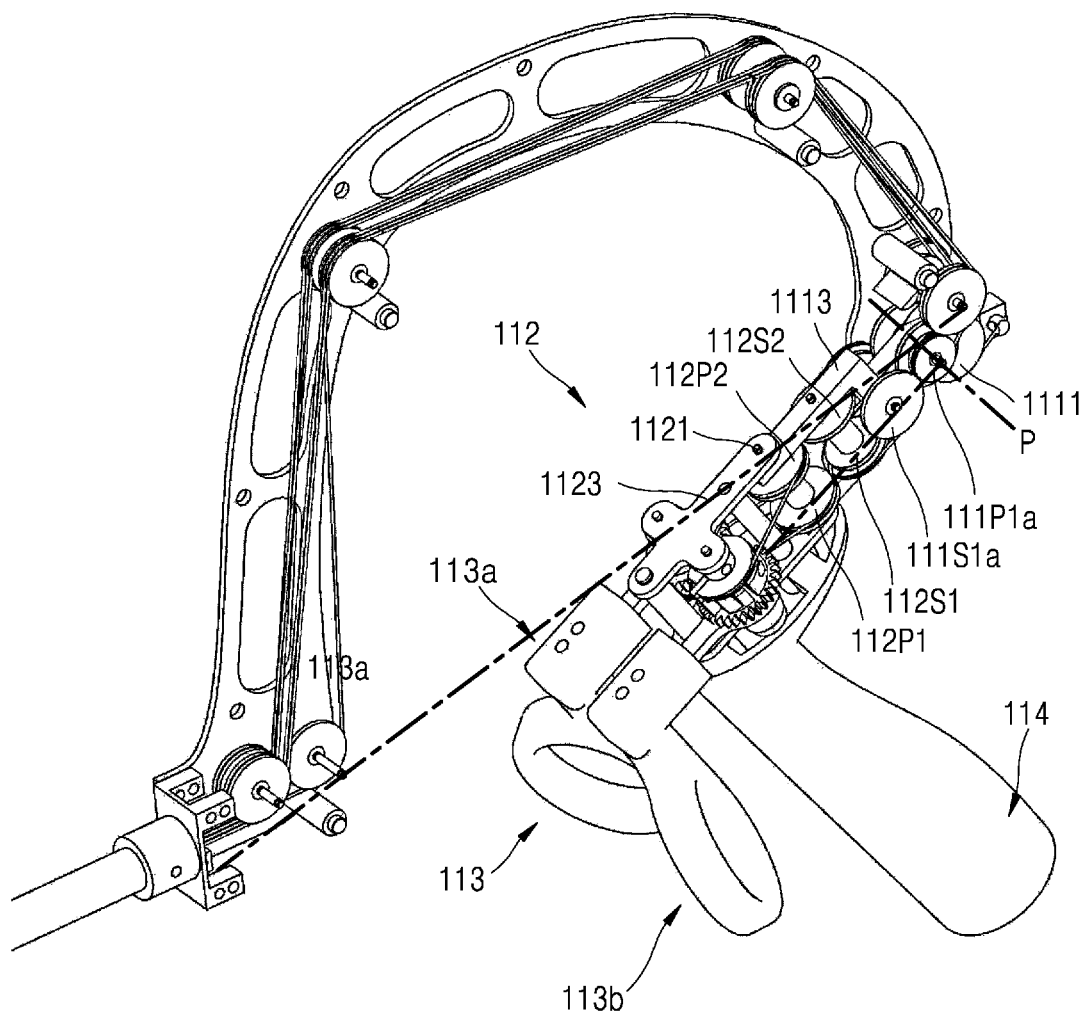
FIG. 18 is a perspective view of the pitch motion of the surgical instrument of FIG. 12.

FIGS. 17A-17B schematically illustrate a configuration of pulleys and wires related to a pitch motion of the surgical instrument 100 of FIG. 12 according to an embodiment of the disclosure, for a first jaw and a second jaw. FIG. 17A illustrates pulleys and wires only for the second jaw, and FIG. 17B illustrates pulleys and wires only for the first jaw. As illustrated in FIG. 14, two pulleys for each wire are related to the pitch motion and both strands of each wire are wound in the same path, and thus both strands are expressed by a single line in FIGS. 17A and 17B. FIG. 18 is a perspective view of the pitch motion of the surgical instrument of FIG. 12.

Referring to FIG. 17B, when the first handle 114 is rotated around the pitch rotation shaft 1111 in an arrow OPP1 direction, the first actuation pulley 113P1, the first jaw pitch auxiliary pulleys 111S1*a* and 111S1*b*, and the first jaw pitch pulleys 111P1*a* and 111P1*b*, and the first jaw wire 130J1 wound therearound, are rotated as a whole around the pitch rotation shaft 1111. At this time, as illustrated in FIG. 14, as both strands of the first jaw wire 130J1 are wound around the upper sides of the first jaw pitch pulleys 111P1*a* and 111P1*b*, both strands are moved in a direction toward an arrow W1. Consequently, as described in FIG. 5, the first jaw 121 of the end tool 120 is rotated in an arrow EPP1 direction.

Referring to FIG. 17A, when the first handle 114 is rotated around the pitch rotation shaft 1111 in an arrow OPP2 direction, the second actuation pulley 113P2, the second jaw pitch auxiliary pulleys 111S2*a* and 111S2*b*, and the second jaw pitch pulleys 111P2*a* and 111P2*b*, and the second jaw wire 130J2 wound therearound, are rotated as a whole around the pitch rotation shaft 1111. In this state, as described in FIG. 14, both strands of the second jaw wire 130J2 are wound around the lower sides of the second jaw pitch pulleys 111P2*a* and 111P2*b*, both strands are moved in a direction toward an arrow W2. Consequently, as described in FIG. 5, the second jaw 122 of the end tool 120 is rotated in an arrow EPP2 direction.

Accordingly, FIGS. 12 and 13 illustrating an embodiment may describe the motion principle through FIGS. 14, 15A-15B, 16, 17A-17B, and 18, and the actuation motion, the yaw motion, and the pitch motion may be independently manipulated.

As described in FIG. 1, as the rotation shafts of each of the actuation manipulation portion 113, the yaw manipulation portion 112, and the pitch manipulation portion 111 are located at the rear of each manipulation portion, the manipulation portion 110 is configured to have the same joint configured of the end tool, so that a user may perform intuitively matching manipulations.

In particular, in the surgical instrument 100 according to an embodiment of the disclosure, a pulley is provided at each joint point (actuation joint, yaw joint, or pitch joint), a wire (first jaw wire or second jaw wire) is wound around the pulley, a rotation manipulation (actuation rotation, yaw rotation, or pitch rotation) of a manipulation portion causes a movement of each wire, and thus a desired motion of the end tool 120 is induced Furthermore, as auxiliary pulleys may be provided at one side of each pulley, the auxiliary pulleys may prevent the wire from being wound around one pulley multiple times. Accordingly, the wires wound around the pulleys do not contact each other, and the paths of the wire being wound around the pulley and the wire being released from the pulley are safely formed so that safety and efficiency in the transmission of a driving force of a wire may be improved.

As described above, the yaw manipulation portion 112 and the actuation manipulation portion 113 are directly formed on the first handle 114. Accordingly, when the first handle 114 is rotated around the pitch rotation shaft 1111, the yaw manipulation portion 112 and the actuation manipulation portion 113 are also rotated together with the first handle 114. Accordingly, the coordinate systems of the yaw manipulation portion 112 and the actuation manipulation portion 113 are not fixed, but are continuously changed relative to the rotation of the first handle 114. In other words, FIG. 2 illustrates that the yaw manipulation portion 112 and the actuation manipulation portion 113 are parallel to the Z-axis. However, when the first handle 114 is rotated, the yaw manipulation portion 112 and the actuation manipulation portion 113 are not parallel to the Z-axis any longer. In other words, the coordinate systems of the yaw manipulation portion 112 and the actuation manipulation portion 113 are changed according to the rotation of the first handle 114. However, in the present specification, for convenience of explanation, unless described otherwise, the coordinate systems of the yaw manipulation portion 112 and the actuation manipulation portion 113 are described on the basis of a state in which the first handle 114 is located perpendicularly to the connection portion 140 as illustrated in FIG. 2.

As such, While the disclosure has been particularly shown and described with reference to preferred embodiments using specific terminologies, the embodiments and terminologies should be considered in descriptive sense only and not for purposes of limitation. Therefore, it will be understood by those of ordinary skill in the art that various changes in form and details may be made therein without departing from the spirit and scope of the disclosure as defined by the following claims.

INDUSTRIAL APPLICABILITY

The present disclosure provides an end tool of a surgical instrument and a surgical instrument having the same. Furthermore, the embodiments of the present disclosure may be applied to manually operated surgical instruments for use in industrially used laparoscopic surgery or various surgical procedures.

The invention claimed is:

1. An end tool of a surgical instrument, the end tool comprising:
    a first jaw and a second jaw capable of rotating independently of each other;
    a J11 pulley coupled to the first jaw and formed to be capable of rotating around a first axis;
    a J21 pulley coupled to the second jaw and formed to be capable of rotating around an axis that is substantially the same as or parallel to the first axis;
    an end tool hub comprising a pair of jaw pulley coupling portions formed to face each other and a guide portion connecting the pair of jaw pulley coupling portions, wherein at least parts of the J11 pulley and the J21 pulley are accommodated in a space formed by the pair of jaw pulley coupling portion and the guide portion, and a region adjacent to the J11 pulley and the J21 pulleys in the guide portion has a section that is curved with a certain radius of curvature, the section being on a plane perpendicular to the first axis;
    a J12 pulley and a J14 pulley formed at one side of the end tool hub to be capable of rotating around a second axis forming an angle with respect to the first axis;
    a J22 pulley and a J24 pulley formed at one side of the end tool hub to be capable of rotating around an axis that is substantially the same as or parallel to the second axis; and the guide portion is integrally formed with the pair of jaw pulley coupling portions as one body, wherein a first jaw wire sequentially contacts the J12 pulley, the J11 pulley, the guide portion, and the J14 pulley, and a second jaw wire sequentially contacts the J22 pulley, the J21 pulley, the guide portion, and the J24 pulley, wherein two strands of the first jaw wire wound around the J11 pulley are disposed by the guide portion at one side with respect to a plane perpendicular to the second axis and passing through the first axis, and wherein two strands of the second jaw wire wound around the J21 pulley are disposed by the guide portion at another side with respect to the plane perpendicular to the second axis and passing through the first axis.

2. The end tool of claim 1, wherein
the first jaw wire is wound around the J11 pulley in a first direction and then wound around the guide portion in a second direction that is opposite to the first direction, and
the second jaw wire is wound around the J21 pulley in the second direction and then wound around the guide portion in the first direction.

3. The end tool of claim 2, wherein
a connection portion hub capable of rotating around the second axis with respect to the end tool hub is formed at one side of the end tool hub, and
in the connection portion hub,
a J13 pulley and a J15 pulley are formed to be capable of rotating around an axis that is substantially parallel to the second axis, and
a J23 pulley and a J25 pulley are formed to be capable of rotating around the axis that is substantially parallel to the second axis.

4. The end tool of claim 3, wherein
the first jaw wire is wound around the J13 pulley in a third direction and then wound around the J12 pulley in a fourth direction that is opposite to the third direction, and
the second jaw wire is wound around the J23 pulley in the fourth direction and then wound around the J22 pulley in the third direction.

5. The end tool of claim 4, wherein the first direction and the third direction are substantially perpendicular to each other.

6. The end tool of claim 1, wherein
the first jaw wire is located on an inner tangent line of the J11 pulley and the guide portion, and a rotation angle of the J11 pulley is increased by the guide portion, and
the second jaw wire is located on an inner tangent line of the J21 pulley and the guide portion, and a rotation angle of the J21 pulley is increased by the guide portion.

7. The end tool of claim 1, wherein
the first jaw wire is fixedly coupled to the J11 pulley by a fixing coupling portion, and
the second jaw wire is fixedly coupled to the J21 pulley by another fixing coupling portion.

8. The end tool of claim 1, wherein
the first jaw wire passes inwardly through the J11 pulley and the guide portion, and
the second jaw wire passes inwardly through the J21 pulley and the guide portion.

9. The end tool of claim 1, wherein one or more guide grooves are further formed in the guide portion as a surface of the guide portion is recessed to accommodate at least a part of each of the first jaw wire or the second jaw wire.

10. The end tool of claim 9, wherein the guide groove is formed only in a part of the guide portion.

11. The end tool of claim 1, wherein the guide portion is disposed at a side opposite to the first jaw and second jaw with respect to the J11 pulley and the J21 pulley.

12. The end tool of claim 1, wherein the pair of jaw pulley coupling portions and the guide portion connecting the pair of jaw pulley coupling portions have a "Π" shape.

13. The end tool of claim 1,
wherein the guide portion is formed in a direction of the first axis, and
wherein the pair of jaw pulley coupling portions extend from both end portions of the guide portion in a third axis direction that is different from each of the first axis and the second axis.

14. The end tool of claim 13, wherein at least a part of a section of the guide portion has an arc shape in a direction perpendicular to the first axis.

15. The end tool of claim 1, wherein in the guide portion, surfaces facing the J11 pulley and the J21 pulley protrude toward the J11 pulley and the J21 pulley to a predetermined degree.

16. The end tool of claim 1, wherein
the J12 pulley and J14 pulley are disposed at one side with respect to a plane perpendicular to the second axis and passing through the first axis, and
the J22 pulley and J24 pulley are disposed at another side with respect to the plane perpendicular to the second axis and passing through the first axis.

17. The end tool of claim 1, wherein a first jaw wire and a second jaw wire contact at least a part of the guide portion.

* * * * *